United States Patent [19]

Cragoe, Jr. et al.

[11] 4,177,285
[45] Dec. 4, 1979

[54] [1-OXO-2-THIENYL-2-SUBSTITUTED-5-INDANYLOXY (OR THIO)]ALKANOIC ACIDS AND DERIVATIVES THEREOF

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 889,161

[22] Filed: Mar. 23, 1978

Related U.S. Application Data

[60] Division of Ser. No. 585,434, Jun. 10, 1975, Pat. No. 4,096,267, which is a continuation-in-part of Ser. No. 492,651, Jul. 30, 1974, abandoned, which is a continuation-in-part of Ser. No. 405,736, Oct. 11, 1973, abandoned.

[51] Int. Cl.$^2$ .................. A61K 31/125; C07D 333/10
[52] U.S. Cl. ..................................... 424/275; 549/77; 549/78; 549/79
[58] Field of Search ................. 260/332.2 A; 424/275

[56] References Cited

U.S. PATENT DOCUMENTS

3,984,465  10/1976  Cragoe et al. .................. 260/520 C

FOREIGN PATENT DOCUMENTS

7213847  3/1977  Sweden .............................. 260/308 D
1373318  11/1974  United Kingdom ................ 260/308 D

*Primary Examiner*—Frederick E. Waddell
*Attorney, Agent, or Firm*—Michael C. Sudol, Jr.

[57] ABSTRACT

[1-Oxo-2-aryl or thienyl-2-substituted-5-indanyloxy (or thio)]alkaoic acid, derivatives thereof, their salts, esters and amides are disclosed. The products display a dual pharmaceutical utility in that they exhibit diuretic, saluretic and uricosuric activity. Also disclosed are processes for the preparation of such [1-oxo-2-aryl or thienyl-2-substituted-5-indanyloxy (or thio)]alkanoic acids, pharmaceutical compositions comprising therapeutically effective amounts of such compounds and methods of treatment comprising administering such compounds and compositions.

18 Claims, No Drawings

[1-OXO-2-THIENYL-2-SUBSTITUTED-5-INDANYLOXY (OR THIO)]ALKANOIC ACIDS AND DERIVATIVES THEREOF

CROSS REFERENCE TO RELATED APPLICATIONS

This is a divisional of application Ser. No. 585,434 filed June 10, 1975, now U.S. Pat. No. 4,096,267 issued June 20, 1978, which is a continuation-in-part of our co-pending application Ser. No. 492,651, filed July 30, 1974, now abandoned, which in turn is a continuation-in-part of our co-pending application Ser. No. 405,736 filed Oct. 11, 1973, now abandoned.

BACKGROUND OF THE INVENTION

This invention relates to a new class of compounds which can generally be described as [1-oxo-2-aryl or thienyl-2-substituted(and 2-aryl-2,3-disubstituted)-7- (and 6,7-disubstituted)-5-indanyloxy(or thio)]alkanoic acids, 5-tetrazolyl analogues of such acids, and to the non-toxic pharmacologically acceptable salt, ester and amide derivatives thereof. These compounds will collectively be referred to herein as "[1-oxo-2-aryl or thienyl-2-substituted-5-indanyloxy(or thio)]alkanoic acids" or more simply as "2-aryl or thienyl substituted indanones" for convenience. Further, this invention relates to a process for the preparation of such 2-aryl or thienyl substituted indanones, to pharmaceutical compositions comprising therapeutically effective amounts of such compounds and to methods of treatment comprising administering such compounds and compositions.

Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration when administered in therapeutic dosages to patients in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients requiring diuretic and saluretic treatment without incurring the risk of inducing gout. In fact, when used in appropriate doses, the compounds of this invention function as uricosuric agents.

Thus, it is an object of the present invention to provide 2-aryl or thienyl substituted indanones of the above general description and to provide processes for the preparation thereof.

A further object of this invention is to provide pharmaceutical compositions comprising therapeutically effective amounts of such 2-aryl or thienyl substituted indanones and to provide a method of treatment comprising administering such compounds and compositions.

DETAILED DESCRIPTION OF THE INVENTION

The 2-aryl or thienyl substituted indanones of the present invention have the following structure:

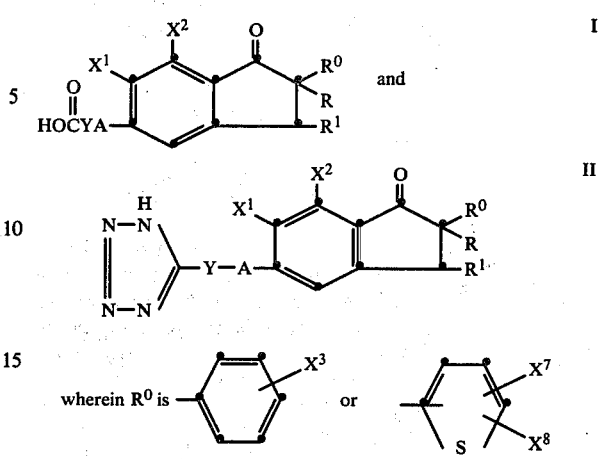

wherein $X^3$ is hydrogen, halogen such as chloro, bromo, fluoro, or iodo, lower alkyl such as methyl, ethyl, n-propyl, n-butyl, tertiary butyl, n-pentyl and the like; cycloalkyl such as cyclopentyl or cyclohexyl; lower alkoxy having from 1 to 5 carbon atoms such as methoxy, nitro, hydroxy, amino, cyano, aminomethyl, sulfamoyl, methanesulfonyl or chlorosulfonyl, acylamino such as acetamido, acylaminomethyl, such as chloroacetylaminomethyl; $X^7$ is hydrogen, loweralkyl having from 1 to 5 carbon atoms such as methyl, halogen such as chloro, bromo, fluoro or iodo, or aminomethyl; and $X^8$ is hydrogen or lower alkyl having from 1 to 5 carbon atoms such as methyl; and wherein A is oxygen or sulfur; R is lower alkyl containing from 1 to 5 carbon atoms such as methyl, ethyl, n-propyl, isopropyl, n-butyl, isobutyl, tert-butyl, pentyl and the like; cycloalkyl, for example, cycloalkyl containing from 3 to 6 carbon atoms such as cyclopentyl, cyclohexyl and the like; cycloalkyl lower alkyl such as cyclopropylmethyl, cyclopentylmethyl and the like, lower alkenyl containing from 3 to 5 carbon atoms such as allyl, 1,2- or 3-butenyl, 1,2,3- or 4-pentenyl and the like; phenyl lower alkyl wherein the lower alkyl moiety contains from 1 to 3 carbon atoms such as benzyl, phenethyl, phenylpropyl and the like, phenyl lower alkenyl such as cinnamyl and the like; aryl or substituted aryl such as phenyl, halo-aryl, lower alkylaryl, or lower alkoxyaryl or thienyl and the like; $R^1$ is hydrogen, lower alkyl, or aryl such as phenyl; and wherein R and $R^1$ taken together with the carbon atoms to which they are attached may form a hydrocarbylene ring containing from 3 to 6 carbon atoms; and wherein $X^1$ is hydrogen, methyl or halo, such as chloro, bromo, fluoro and the like; $X^2$ is methyl, trihalomethyl or halo such as chloro, bromo, fluoro, and the like; or $X^1$ and $X^2$ may be joined to form a hydrocarbylene chain containing from 3 to 4 carbon atoms, for example, trimethylene, tetramethylene, 1,3-butadienylene and the like; and wherein Y is an alkylene or haloalkylene radical having from 1 to about 4 carbon atoms between the oxy (or thio) and the carboxy group, for example, methylene, ethylene, propylidene, isopropylidene, isobutylidene, fluoromethylene, and the like; and the nontoxic pharmaceutically acceptable salt, amide, anhydride and ester derivatives thereof.

The preferred compounds of this invention are those compounds of Formulae I and II, above wherein A is oxygen, Y is methylene and R, $R^o$, $R^1$, $R^2$, $X^1$, $X^2$, $X^3$, $X^7$ and $X^8$ are as defined above.

Preferred compounds of this invention are those compounds of Formula I above wherein A is oxygen; Y is methylene: R⁰ is

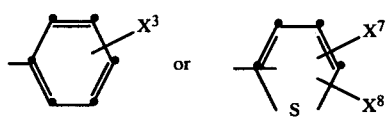

R¹ is hydrogen; R is lower alkyl containing from 1 to 5 carbon atoms and cyclo alkyl containing from 3 to 6 carbon atoms; $X^1$ and $X^2$ are selected from the group consisting of chloro and methyl; $X^3$ is hydrogen, nitro, hydroxy, lower alkyl (C 1-5 carbon atoms), lower alkoxy (C 1-5 carbon atoms), halo, amino, cyano or aminomethyl; $X^7$ is hydrogen or lower alkyl (C 1-5 carbon atoms); $X^8$ is hydrogen; and the non-toxic, pharmaceutically acceptable salts and ester derivatives thereof.

Particularly preferred compounds of this invention are 1-oxo-2-aryl-2-substituted-6,7-disubstituted-5-indanyloxyacetic acids, and the non-toxic pharmacologically acceptable salts thereof, having the following structure:

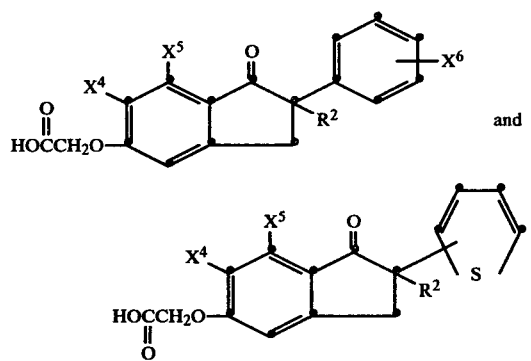

wherein $R^2$ is lower alkyl containing from 1 to 3 carbon atoms such as methyl, ethyl, n-propyl or isopropyl, or cycloalkyl containing 3 to 6 carbon atoms such as for example cyclopropyl, cyclopentyl or cyclohexyl; $X^4$ and $X^5$ are the same or different radicals selected from methyl or chloro; and $X^6$ is hydrogen, methyl, chloro or fluoro and the nontoxic pharmaceutically acceptable salts thereof.

Still more preferred compounds of this invention are those of Formula Ia above wherein $R^2$ is lower alkyl containing from 1 to 3 carbon atoms, $X^4$ and $X^5$ are both chloro and $X^6$ is hydrogen, methyl, chloro or fluoro and the non-toxic pharmaceutically acceptable salts thereof.

Finally, still more preferred compounds of this invention are those described in the previous paragraph wherein
 (a) $R^2$ is methyl;
 (b) wherein $R^2$ is methyl and $X^6$ is in the para position; and
 (c) those compounds of (b) excluding the 2-(thienyl-)indanone Also a particular group of preferred compounds of this invention are those of Formula I, II and Ia and the preferred and particularly preferred compounds of Formula I and Ia wherein $X^1$ and $X^2$ or $X^4$ and $X^5$ are both chloro.

The foregoing class of compounds exhibits particularly good diuretic/saluretic activity. Such compounds also either maintain the uric acid concentration of the body at pretreatment levels or even cause a decrease in uric acid concentration.

Several methods may be employed to prepare the 2-aryl or 2-thienyl substituted indanones of this invention. One method comprises 2-alkylation of a [1-oxo-2-aryl or 2-thienyl-5-indanyloxy(or thio)]alkanoic acid or ester of structure III (infra) with an alkylating agent of the formula RZ wherein Z is halo. This reaction is conducted by first treating the [1-oxo-2-aryl or 2-thienyl-5-indanyloxy(or thio)]alkanoic acid or ester with a suitable base for example an alkali metal hydride such as sodium hydride and the like or an alkali metal alkoxide for example potassium tertiary butoxide, sodium methoxide and the like, or alkali metal amides such as sodium amide, lithium amide and the like. The resulting carbanion is then treated with the alkylating agent, RZ. Any solvent which is inert or substantially inert to the reactants employed may be used. Suitable solvents include for example, 1,2-dimethoxyethane, tertiary butanol, benzene, dimethylformamide and the like. The reaction may be conducted at a temperature in the range of from about 0° C. to about 150° C. In general, the reaction is conducted at a temperature in the range of from about 0°–50° C. The following equation illustrates this process:

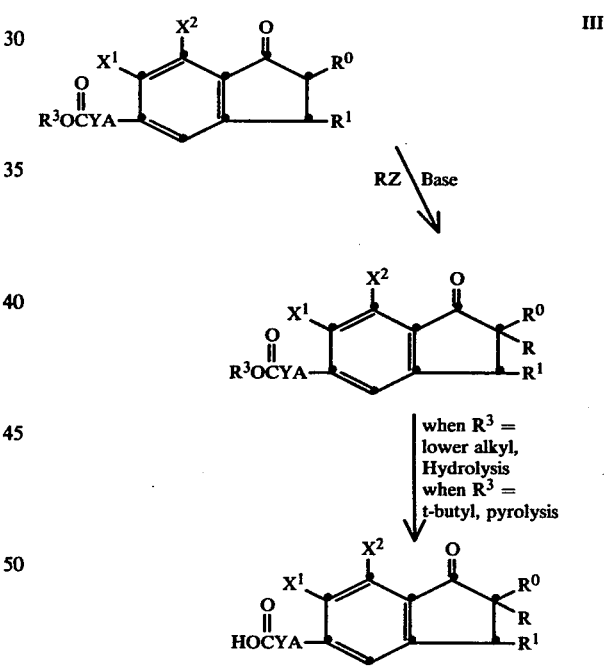

wherein A, R, R⁰, $R^1$, $X^1$, $X^2$, $X^3$, $X^7$, $X^8$, Z and Y are as defined above and $R^3$ is hydrogen or lower alkyl.

A second method for preparing the [1-oxo-2-aryl-2-substituted-5-indanyloxy(or thio)]alkanoic acids of this invention comprises reacting a halo alkanoic acid or ester thereof,

with a suitable 2-aryl or 2-thienyl-2-substituted-5-hydroxy(or mercapto)-1-indanone (IV):

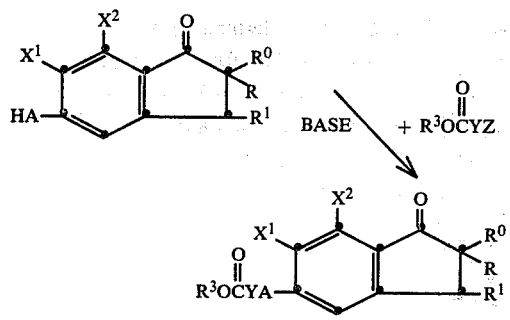

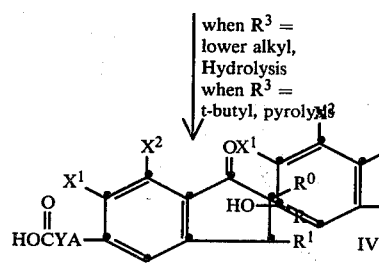

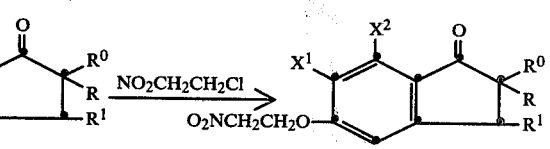

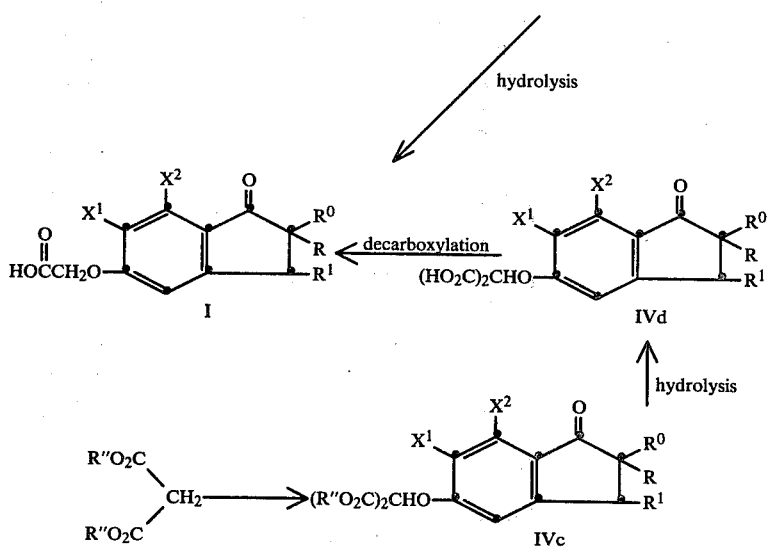

wherein all substituents are as defined above.

In general, the reaction is conducted in the presence of a base such as an alkali metal carbonate, hydroxide or alkoxide such as potassium carbonate, sodium carbonate, potassium hydroxide, sodium hydroxide, sodium methoxide and the like. Any solvent which is inert or substantially inert to the reactants and in which the reagents are reasonably soluble may be employed. Acetone, ethanol and dimethylformamide for example have proven to be particularly advantageous solvents. The reaction may be conducted at a temperature in the range of from about 25° C. to the reflux temperature of the particular solvent employed. If the haloalkanoic acid ester is employed, the ester obtained may be hydrolyzed to the free acid by methods well-known to those skilled in the art. When $R^3$ is the tert-butyl group, the acid may be obtained by acid catalyzed pyrolysis, such as by heating the tert-butyl ester in the presence of a strong acid, for example, in the presence of p-toluenesulfonic acid, sulfuric acid, gaseous hydrogen chloride, and the like. In general, pyrolysis is effected by heating at a temperature in the range from about 70°–140° C., preferably 80°–100° C. Also, the pyrolysis may be conducted without a solvent or in the presence of a suitable non-aqueous medium in which the reactants are reasonably soluble, for example, in the presence of benzene, toluene, xylene and the like.

Two additional processes for preparing compounds of Formula I are as illustrated by the following flow diagram:

The first process shown involves reacting a 5-hydroxy (or mercapto) compound (IVa infra) with halonitro ethane to form a 2-nitroethane intermediate (Formula IVb) which intermediate upon hydrolysis yields the end product (I). The preparation of the intermediate of Formula IVb is shown in British Pat. No. 1,325,528.

In the other process shown, the 5-hydroxy (or mercapto) compound (IVa infra) is reacted with a malonic ester (wherein R" is loweralkyl, preferably ethyl) to form a malonic ester intermediate (IVc) which intermediate is hydrolyzed to form another intermediate (Formula IVd) which latter compound is then decarboxylated to form the end product I.

Those 2-aryl or 2-thienyl substituted indanones of this invention wherein the alkylene chain, Y, contains 2-linear carbon atoms between the carboxy and oxy (or thio) groups are prepared from the corresponding 5-hydroxy (or mercapto) compounds (IV infra) by the reaction of the latter with propiolactone or with an appropriately substituted propiolactone in the presence of a base such as an aqueous solution of sodium hydroxide, preferably while heating the solution at reflux temperatures followed by the acification of the carboxylate intermediate thus formed to the desired acid. The following equation illustrates the reaction:

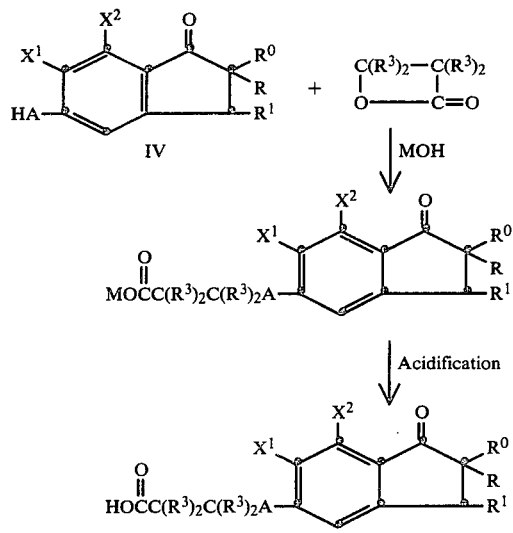

wherein all substituents are as defined above and M is a cation derived from an alkali metal hydroxide or alkali metal carbonate such as sodium or potassium cation.

The 2-aryl or 2-thienyl-2-substituted-5-hydroxy(or mercapto)-1-indanones (IV, supra) which also exhibit diuretic, saluretic and uricosuric activity and which are novel compounds themselves are prepared by treating the correspondingly substituted 2-aryl or 2-thienyl-2-substituted-5-lower alkoxy or aralkoxy (or lower alkyl or aralkyl thio)-1-indanone with an ether cleaving reagent such as aluminum chloride, pyridine hydrochloride, sodium in liquid ammonia, and the like. When aluminum chloride is employed the solvent may be heptane, carbon disulfide, methylene chloride and the like. When pyridine hydrochloride is employed, it is not necessary to employ a solvent. Those 2-aryl substituted indanones of the present invention wherein the aryl substituent, $X^3$, is hydroxy are conveniently prepared by treating the corresponding acid and tetrazole (Formula I and II, supra) wherein the aryl substituent, $X^3$, is methoxy, with hydrogen bromide in acetic acid.

A preferred method for preparing the 5-hydroxy or 5-mercapto compounds of Formula IV(supra) wherein the aryl substituent, $X^3$, is a lower alkoxy radical consists of hydrogenolysis of the corresponding 5-aralkoxy (or thio) compound. The hydrogenolysis reaction is conveniently conducted in a hydrogenation apparatus in a solvent such as methanol, ethanol, acetic acid, and the like, in the presence of a catalyst such as 5% palladium on carbon or platinum on carbon at a pressure of from about 1.0 to about 40 atmospheres.

2-Arylation or 2-thienylation to obtain the 5-lower alkoxy or 5aralkoxy (or lower alkyl thio or aralkyl thio) compounds V (infra), which also exhibit diuretic, saluretic, and uricosuric activity is effected by treating the corresponding 2-substituted compound VI with a suitable reagent such as a diphenyl iodonium salt (when $R^o$ is phenyl, substituted phenyl) or thienyl of the formula:

$[R^o]_2IZ$ wherein $R^o$, $X^3$ and z are as defined above.

This reaction is conducted by first treating the 2-substituted compound VI with a suitable base, for example an alkali metal hydride such as sodium hydride and the like, an alkali metal akoxide, for example sodium methoxide, potassium tertiary butoxide and the like; or an alkali metal amide such as sodium amide, lithium amide and the like. The resulting carbanion is then treated with the arylating agent. Any solvent which is inert or substantially inert to the reactants employed may be used; suitable solvents include, for example, 1,2-dimethoxyethane, tertiary butanol, benzene, dimethylformamide and the like. The reaction may be conducted at a temperature in the range of from about 25°–150° C. The following equation illustrates this process:

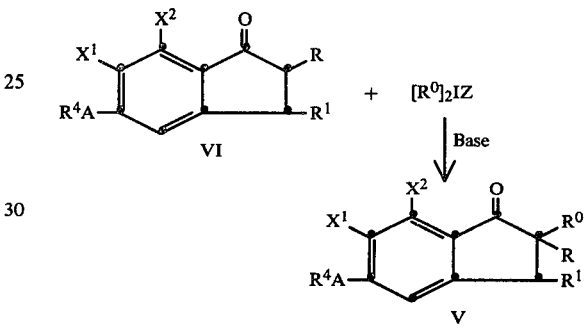

wherein all substituents are as defined above and $R^4$ is lower alkyl or aralkyl. The t-lower alkoxy or 5-aralkoxy (or lower alkyl thio or aralkyl thio) reactants (VI, supra) employed in this particular procedure may be obtained by well-known etherification methods of the corresponding 5-hydroxy (or mercapto) indanones, which are known compounds and are described in U.S. Pat. Nos. 3,668,241 and 3,704,314.

A second method for preparing the ethers of formula V (supra) comprises 2-alkylation of the corresponding 2-aryl or 2-thienyl compound VII (infra) with a suitable alkylating agent of the formula, RZ, wherein R and Z are as defined above. This reaction is conducted by first treating the 2-aryl or 2-thienyl compound (VII) with a suitable base, for example, an alkali metal hydride such as sodium hydride and the like, an alkali metal alkoxide, for example, sodium methoxide, potassium tertiary butoxide and the like, or an alkali metal amide such as sodium amide, lithium amide and the like. The resulting carbanion is then treated with the alkylating agent, RZ. Any solvent which is inert or substantially inert to the reactants employed may be used. Suitable solvents include for example 1,2-dimethoxyethane, tertiary butanol, benzene, dimethylformamide and the like. The reaction may be conducted at a temperature in the range of about 0° to 150° C. The following equation illustrates this process.

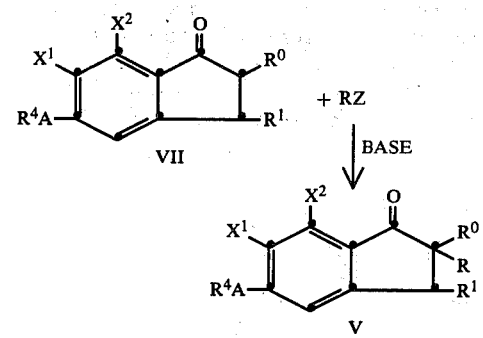

wherein all substituents are as described above.

One method for preparing the indanone intermediate (VIa, infra) useful in the preparation of the 2-aryl substituted indanones of this invention comprises the cyclialkylation of a 4-lower alkoxy (or lower alkyl thio) substituted [2-alkylidenealkanoyl (or 2-alkylidenearalkanoyl)]benzene (VIII) by treatment with a Lewis acid such as concentrated sulfuric acid, polyphosphoric acid, boron trifluoride and the like. The reaction may be conducted at a temperature in the range of from about 0° to about 60° C. The following equation illustrates this process:

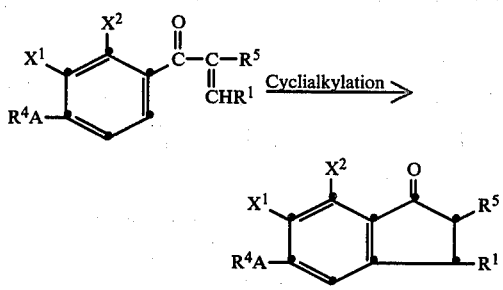

wherein $R^5$ is the substituted phenyl group of formula I or is R, as previously defined, and all other substituents have been defined.

The 4-lower alkoxy (and lower alkyl thio)-substituted [(2-alkylidenealkanoyl) (or 2-alkylidene)]aralkanoyl)]-benzenes (VIII, supra) employed may be prepared by several methods. One method, limited to the preparation of the nuclear lower alkoxy (and lower alkyl thio)-4-(2-methylenealkanoyl) (and 2-methylenearalkanoyl)-benzenes (VIIa, infra) comprises treating a nuclear lower alkoxy-(or lower alkyl thio)-4-alkanoylbenzene (or 4-aralkanoylbenzene) (IX) with dimethylamine hydrochloride and paraformaldehyde followed by treatment of the Mannich intermediate (IXa), thus obtained, with aqueous sodium bicarbonate or anhydrous dimethylformamide, either with or without heat, to afford the desired compound, (VIIIa). The following equation illustrates this process:

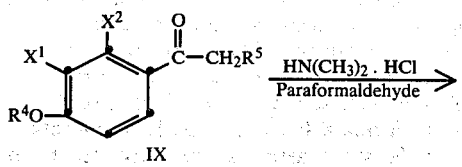

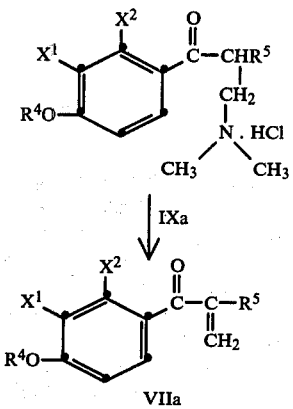

wherein all substituents are as defined above.

A second method for preparing the 4-lower alkoxy-(and lower alkyl thio) substituted (2-alkylidenealkanoyl)-benzenes wherein $R^1$ is methyl, comprises treating a 4-lower alkoxy-(or lower alkyl thio) substituted 2-bromo-2-methylpropionylbenzene (X, infra) with a dehydrobrominating agent such as lithium bromide, lithium chloride and the like. Suitable solvents for this reaction include dimethylformamide and the like. This reaction is conveniently conducted at a temperature in the range of from about 50° to about 120° C. The following equation illustrates this reaction:

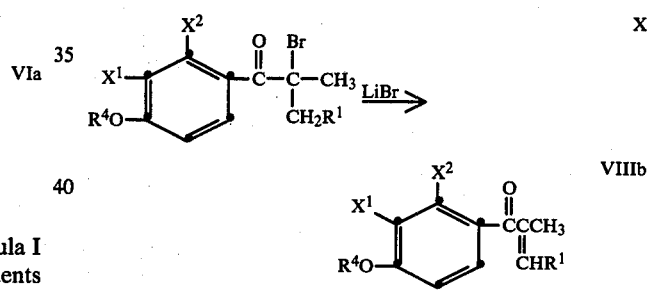

wherein all substituents are as defined above.

A third method for preparing the 4-lower alkoxy (and lower alkyl thio) [2-alkylidenealkanoyl (or 2-alkylidenaralkanoyl)]benzenes (VIIc) comprises treating a 4-lower alkoxy (or lower alkyl thio) substituted alkanoyl or aralkanoylbenzene (IXa) with a methylene inserting reagent such as a bis-dimethylaminomethane in the presence of an alkanoic acid anhydride such as acetic anhydride. The reaction is conducted at a temperature of from about 25° to about 50° C. Any solvent which is inert or substantially inert to the reactants employed may be used, but in general the methylene inserting reagent, such as bis-dimethylaminomethane, serves as the solvent medium. The following equation illustrates this process:

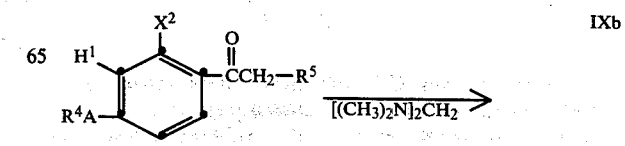

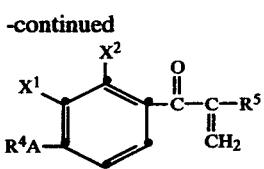

wherein all substituents are as defined above.

The [4-lower alkoxy (and lower alkyl thio)-substituted]alkanoyl and aralkanoylbenzenes (IXb) are either known compounds or may be prepared by the reaction of an alkanoyl halide or aralkanoyl halide with a nuclear lower alkoxy (or lower alkyl thio) substituted benzene (XI), in the presence of a Friedel-Crafts catalyst such as aluminum chloride and the like. The reaction solvent and the temperature at which the reaction is conducted are not critical aspects of this reaction inasmuch as any solvent which is inert to the acyl halide and nuclear lower alkoxy (or lower alkyl thio) substituted benzene may be employed with good results. In this regard, it has been found that methylene chloride and carbon disulfide are particularly suitable solvents. The following equation illustrates this process:

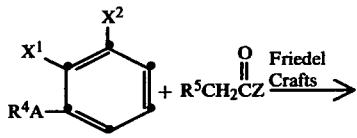

Those compounds of the instant invention wherein R and $R^1$ are joined to form a cyclopropyl ring (XIII, infra) are prepared by treating a (1-oxo-2-indene-5-ylox-y)-alkanoic acid (XII) with an alkali metal base such as sodium hydride and the like followed by treatment with a methylating agent, for example, trimethylsulfoxonium iodide and the like. The (1-oxo-2-indene-5-yloxy)alkanoic acids employed are described in U.S. Pat. No. 3,668,241. The following equation illustrates this process:

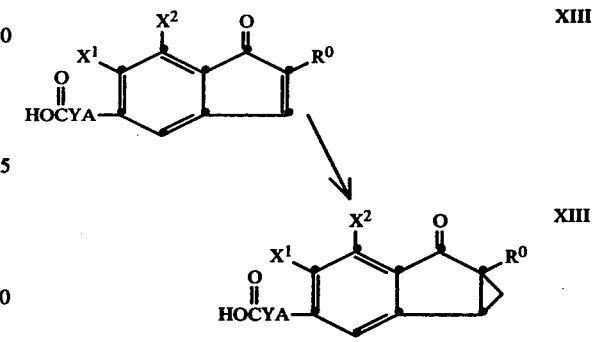

wherein all substituents are as defined above.

The nuclear lower alkoxy precursors of those compounds of the instant invention wherein R and $R^1$ are joined to form a cyclohexyl ring are prepared according to the procedure described in co-pending, commonly assigned application Ser. No. 399,568 filed Sept. 21, 1973 which is incorporated herein by reference:

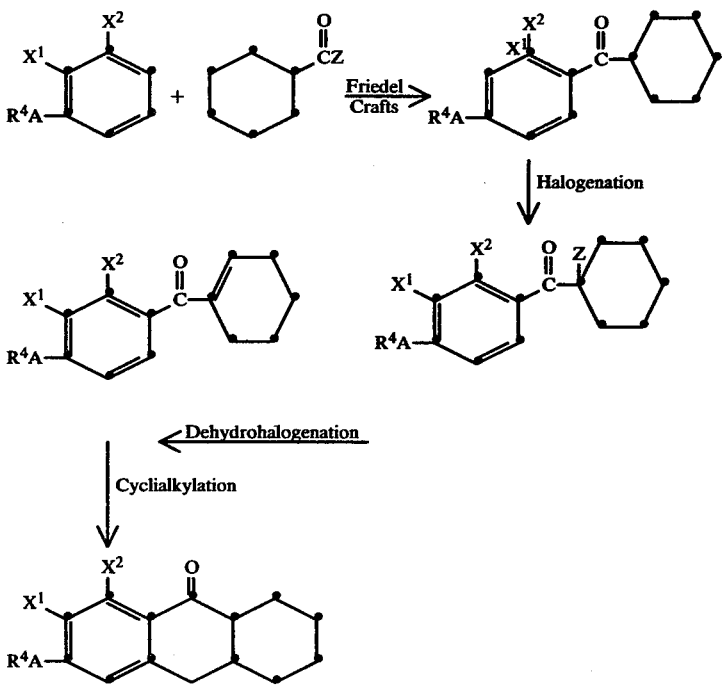

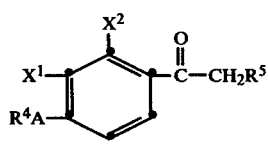

wherein the substituents are as defined above.

Those compounds of Formula I wherein $R^o$ is aryl and the $X^3$ substituents are cyano, chlorosulfonyl, sulfamoyl, nitro, amino or aminomethyl are generally prepared from the compounds of Formula I or an intermediate thereto such as a compound of Formula IV wherein $R^o$ is unsubstituted aryl or thienyl or from a compound of Formula IV or I when $R^o$ is substituted aryl wherein the substituents can be converted to the desired substituent by methods well known in the art. For example, when $R^o$ is unsubstituted aryl the compounds of Formula I can be reacted with chlorosulfonic acid to yield a compound wherein $X^3$ is chlorosulfonyl and the latter compound reacted with ammonia to yield a compound of Formula I wherein $X^3$ is sulfamoyl. Other conversions are shown specifically in the examples, such as for example in Examples 21, 22, 31 & 32A.

As previously mentioned, the non-toxic, pharmacologically acceptable salts of the acids of Formulae I & Ia are within the scope of this invention. These salts include those of alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc. These salts are prepared by conventional methods well known in the art. Thus, the acid upon reaction with alkali metal and alkaline earth metal hydroxides, carbonates, bicarbonates, amines or quarternary ammonium hydroxides, forms the corresponding alkali metal, alkaline earth metal, amine or quaternary ammonium salt.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and the like.

The salts mentioned above are particularly useful as parenteral solutions because they are very soluble in pharmaceutical carriers such as water or alcohol.

The anhydride derived from the carboxylic acids of Formula I are included in the invention.

Also included within the scope of this invention are the ester and amide derivatives of the instant products which are prepared by conventional methods well known to those skilled in the art. Thus, for example, the ester derivatives may be prepared by the reaction of the [1-oxo-2-aryl or 2-thienyl-2-substituted-5-indanyloxy (or thio)]-alkanoic acid of this invention with an alcohol, for example, with a lower alkanol (C 1-5 carbon atoms). The amide derivatives may be prepared by converting a [1-oxo-2-aryl or 2-thienyl-2-substituted-5-indanyloxy (or thio)]-alkanoic acid to its corresponding acid chloride by treatment with thionyl chloride followed by treating said acid chloride with ammonia, an appropriate monolower alkyl amine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and pharmacologically acceptable; said derivatives are the functional equivalent of the corresponding [1-oxo-2-aryl or 2-thienyl-2-substituted-5-indanyloxy (or thio)]alkanoic acids.

In addition to the salts, esters and amides being functionally equivalent to the carboxylic products, those compounds wherein the carboxyl group is replaced by a 5-tetrazolyl radical are also functionally equivalent to the carboxylic acids. These tetrazole analogs are prepared as depicted in the following equation:

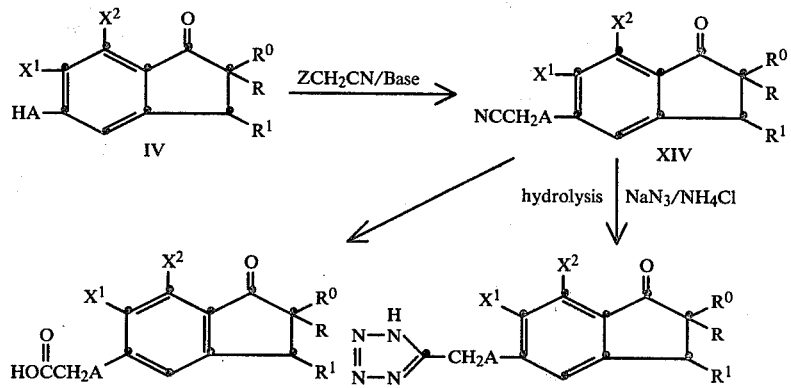

This is Formula I wherein Y is methylene wherein all substituents are as defined above.

The 5-hydroxy (or thio)-1-indanone (IV above) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100° C. to afford the corresponding nitrile (XIV) which, upon treatment with sodium azide and ammonium chloride in dimethylformamide at a temperature in the range of from 25° to 100° C., affords the 5-[1-oxo-2-aryl or 2-thienyl-2-substituted-5-indanyloxy (or thio)methyl]tetrazole.

A still further process for preparing compounds of Formula I (the end product) wherein Y is methylene involves a hydrolysis of the nitrile compound shown in Formula XIV above. This is a typical hydrolysis of a nitrile reaction and is well known to persons skilled in the art.

Many of the instant compounds herein disclosed contain an asymmetric carbon atom in the 2-position of the indanyl ring. When this situation exists, the optical antipodes may be separated by methods described below. This invention embraces, therefore, not only the racemic [1-oxo-2-aryl or 2-thienyl-2-substituted-5-indanyloxy-(or thio)]alkanoic acids but also their opitcally active antipodes.

Separation of the optical isomers of the racemic acids may be accomplished by forming a salt of the racemic mixture with an optically active base such as (+) or (−) amphetimine, (−)-cinchonidine, dehydroabietylamine, (+) or (−)-α-methylbenzylamine, (+) or (−)-α-(1-naphthyl)ethylamine, brucine or strychnine and the like in a suitable solvent such as methanol, ethanol, 2-propanol, benzene, acetonitrile, nitromethane, acetone and the like. There is thus formed in the solution two diastereomeric salts one of which is usually more soluble in the solvent than the other. Repetitive recrystallization of the crystalline salt generally affords a pure diastereomer. The optically pure 2-aryl or 2-thienyl indane acid is obtained by acidification of the salt with a mineral acid, extraction into ether, evaporation of the solvent and recrystallization of the optically pure antipode.

The other optically pure antipode may generally be obtained by using a different base to form the diastereomeric salt. It is of advantage to isolate the partially resolved acid from the filtrates of the purification of the one diastereomeric salt and to further purify this substance through the use of another optically active base.

The examples which follow illustrate the 2-aryl and 2-thienyl indane products of the invention and the methods by which they are prepared. However, the examples are illustrative only and it will be apparent to those having ordinary skill in the art that all of the products embraced by Formula I, supra, may also be prepared in an analogous manner by substituting the appropriate starting materials for those set forth in the examples.

EXAMPLE 1

Preparation of (1-Oxo-2-methyl-2-phenyl-6,7-dichloro-5-indanyloxy)acetic acid

Step A: 2,3-Dichloro-5-phenylacetylanisole

To a stirred mixture of 2,3-dichloroanisole (62 g., 0.35 mole), phenylacetyl chloride (54 g., 0.35 mole) and carbon disulfide (250 ml.) is added portionwise aluminum chloride (47 g., 0.35 mole) with cooling at 0°–5° C. The reaction mixture is left at 25° C. for 17 hours, the carbon disulfide removed, and the residue treated with ice-water and concentrated hydrochloric acid (50 ml.) to give 68.8 g. of 2,3-dichloro-5-phenylacetylanisole which melts at 126°–129° C. on crystallization from benzene:cyclohexane, 2:1.

Elemental analysis for $C_{15}H_{12}Cl_2O_2$: Calc.: C, 61.04; H, 4.10; Found: C, 61.46; H, 4.11.

Step B: 2,3-Dichloro-4-(2-phenylacryloyl)anisole

Acetic anhydride (100 ml.) is added dropwise to a suspension of 2,3-dichloro-4-phenylacetylanisole (29.5 g., 0.01 mole) in bis(dimethylamino)methane (100 ml.) under nitrogen with cooling to maintain the reaction mixture temperature below 60° C. The reaction mixture is stirred at 25° C. for 2 hours, and poured into ice water (1500 ml.) to precipitate 7.4 g. of 2,3-dichloro-4-(2-phenylacryloyl)anisole which melts at 87°–89° C.

Elemental analysis for $C_{16}H_{12}Cl_2O_2$: Calc.: C, 62.56; H, 3.94; Found: C, 62.67; H, 4.04.

Step C: 2-Phenyl-5-methoxy-6,7-dichloro-1-indanone 2,3-Dichloro-4-(2-phenylacryloyl)anisole (7.4 g., 0.024 mole) is added portionwise to cold, concentrated sulfuric acid (150 ml.) with stirring. The reaction mixture is stirred in an ice bath for 2 hours, then added dropwise to ice-water to precipitate 3.91 g. of 2-phenyl-5-methoxy-6,7-dichloro-1-indanone which melts at 193°–195° C. upon crystallization from benzene:cyclohexane, 1:2.

Elemental analysis for $C_{16}H_{12}Cl_2O_2$: Calc.: C, 62.56; H, 3.94; Found: C, 62.84; H, 4.00.

Step D: 2-Phenyl-5-hydroxy-6,7-dichloro-1-indanone

A stirred mixture of 2-phenyl-5-methoxy-6,7-dichloro-1-indanone (3.91 g., 0.0127 mole) and pyridine hydrochloride (40 g.) is heated at 190° C. for one hour, then poured into water (600 ml.). The 2-phenyl-5-hydroxy-6,7-dichloro-1-indanone which separates (2.48 g.) melts at 250°–252° C. after recrystallization from ethanol:water, 2:1.

Elemental analysis for $C_{15}H_{10}Cl_2O_2$: Calc.: C, 61.46; H, 3.44; Found: C, 60.94; H, 3.66.

Step E: (1-Oxo-2-phenyl-6,7-dichloro-5-indanyloxy)acetic acid

2-Phenyl-5-hydroxy-6,7-dichloro-1-indanone (5.86 g., 0.023 mole), iodoacetic acid (4.28 g., 0.023 mole), potassium carbonate (3.04 g., 0.022 mole) and acetone (250 ml.) are heated at reflux for 48 hours. The reaction mixture is cooled to 25° C., concentrated in vacuo to give a solid product which is dissolved in water and acidified with 6 N hydrochloric acid to precipitate 6.8 g. of a mixture of (1-oxo-2-phenyl-6,7-dichloro-5-indanyloxy)acetic acid and 2-phenyl-5-hydroxy-6,7-dichloro-1-indanone. The phenol is removed by crystallization with nitromethane. Concentrating the filtrate to dryness in vacuo and triturating with toluene gives 470 mg. of (1-oxo-2-phenyl-6,7-dichloro-5-indanyloxy)acetic acid which melts at 181°–185° C.

Elemental analysis for $C_{17}H_{12}Cl_2O_4$: Calc.: C, 58.14; H, 3.45; Cl, 20.19; Found: C, 58.17; H, 3.54; Cl, 19.94.

Step F: (1-oxo-2-phenyl-2-methyl-6,7-dichloro-5-indanyloxy)acetic acid

A stirred solution of (1-oxo-2-phenyl-6,7-dichloro-5-indanyloxy)acetic acid (0.351 gm., 0.001 mole) in dimethylformamide (7 ml.) is cooled in an ice bath then treated with sodium hydride (0.084 g. of a 57% oil dispersion, 0.002 moles) and stirred for two hours. Methyl iodide (1 ml.) is added and the reaction mixture is stirred at 25° C. for two hours, poured into ice water, and acidified with dilute aqueous hydrochloric acid affording (1-oxo-2-phenyl-2-methyl-6,7-dichloro-5-indanyloxy)acetic acid which melts at 168°–169° C.

EXAMPLE 2

Where in Example 1, Step A, there is substituted for the 2,3-dichloroanisole an equivalent amount of 2-chloro-3-methylanisole, 2,3-dimethylanisole, 3-methylanisole, or 2-methyl-3-chloroanisole, respectively, and Steps B through F are employed as described there is obtained:

(1-oxo-2-phenyl-2,7-dimethyl-6-chloro-5-indanyloxy)acetic acid (1-oxo-2-phenyl-2,6,7-trimethyl-5-indanyloxy)acetic acid (1-oxo-2-phenyl-2,7-dimethyl-5-indanyloxy)acetic acid (1-oxo-2-phenyl-2,6-dimethyl-7-chloro-5-indanyloxy)acetic acid

EXAMPLE 3

Where in Example 1, there is substituted for the phenylacetyl chloride of Step A an equivalent amount of p-methylphenylacetyl chloride, m-methylphenylacetyl chloride, o-chlorophenylacetyl chloride, p-fluorophenylacetyl chloride, and Steps B through F are employed as therein described there is obtained respectively:

[1-oxo-2-methyl-2-(4-methylphenyl)-6,7-dichloro-5-indanyloxy]acetic acid

[1-oxo-2-methyl-2-(3-methylphenyl)-6,7-dichloro-5-indanyloxy]acetic acid

[1-oxo-2-(2-chlorophenyl)-2-methyl-6,7-dichloro-5-indanyloxy]acetic acid

[1-oxo-2-(4-fluorophenyl)-2-methyl-6,7-dichloro-5-indanyloxy]acetic acid

EXAMPLE 4

Where in Example 1, the 2-alkylating agent, methyl iodide, of Step F is replaced by an equivalent amount of ethyliodide, allylbromide, benzylbromide, and cinnamylbromide, respectively, there is obtained, respectively:

(1-oxo-2-ethyl-2-phenyl-6,7-dichloro-5-indanyloxy)acetic acid (1-oxo-2-allyl-2-phenyl-6,7-dichloro-5-indanyloxy)acetic acid (1-oxo-2-benzyl-2-phenyl-6,7-dichloro-5-indanyloxy)acetic acid (1-oxo-2-cinnamyl-2-phenyl-6,7-dichloro-5-indanyloxy)acetic acid

EXAMPLE 5

(1-Oxo-2-methyl-2-phenyl-6,7-dichloro-5-indanyloxy)acetic acid

Step A: 2',3',-Dichloro-4'-methoxyisobutyrophenone

A stirred mixture of 2,3-dichloroanisole (I) (100 g., 0.565 mole) and isobutyryl chloride (II) (66 g., 0.62 mole) in methylene chloride (400 ml.) is cooled to 5° C. and treated with aluminum chloride (83 g., 0.62 mole) during a one-hour period. The reaction mixture is allowed to warm to 25° C. and after 24 hours is poured into ice water (400 ml.) and hydrochloric acid (30 ml.). The organic phase is washed with 5% sodium hydroxide, water, dried over magnesium sulfate and distilled at reduced pressure affording 68 g. of 2',3'-dichloro-4'-methoxyisobutyrophenone (III) which distills at 120°–130° C./0.5 mm.

Elemental analysis for $C_{11}H_{12}Cl_2O_2$: Calc.: C, 53.46; H, 4.89; Found: C, 54.25; H, 5.07.

Step B: 2-Bromo-2',3'-dichloro-4'-methoxyisobutyrophenone

A stirred solution of 2',3'-dichloro-4'-methoxyisobutyrophenone (45 g., 0.183 mole) in acetic acid (150 ml.) is treated during one-half hour with bromine (30 g., 0.187 mole). The reaction mixture is stirred 10 minutes, then poured into ice water (600 ml.) containing sodium bisulfite (2 g.). The 2-bromo-2',3'-dichloro-4'-methoxyisobutyrophenone (IV) which separates (48 g.) melts at 72°–73° C. after recrystallization from hexane.

Elemental analysis for $C_{11}H_{11}BrCl_2O_2$: Calc.: C, 40.52; H, 3.40; Found: C, 40.68; H, 3.38. Step C: 2-Methylene-2',3'-dichloro-4'-methoxypropiophenone A solution of 2-bromo-2',3'-dichloro-4'-methoxyisobutyrophenone (32 g., 0.1 mole) and anhydrous lithium bromide (17.4 g., 0.2 mole) in DMF (200 ml.) is stirred at 95° C. in an inert atmosphere for three hours and poured into ice water (500 ml.). The 2-methylene-2',3'-dichloro-4'-methoxypropiophenone (V) which separates melts at 59° C. after recrystallization from petroleum ether.

Elemental analysis for $C_{11}H_{10}Cl_2O_3$: Calc.: C, 53.90; H, 4.11; Found: C, 53.72; H, 4.11.

Step D: 2-Methyl-5-methoxy-6,7-dichloro-1-indanone

A solution of 2-methylene-2',3'-dichloro-4'-methoxypropiophenone (40 g., 0.163 mole) in concentrated sulfuric acid (75 ml.) is allowed to stand at 25° C. for 24 hours and then is slowly poured into vigorously stirred ice water (500 ml.). The 2-methyl-5-methoxy-6,7-dichloro-1-indanone which separates (40 g.) melts at 129° C. after recrystallization from methylcyclohexane.

Elemental analysis for $C_{11}H_{10}Cl_2O_2$: Calc.: C, 53.90; H, 4.11; Found: C, 53.84; H, 4.00.

Step E: 2-Methyl-2-phenyl-5-methoxy-6,7-dichloro-1-indanone

Potassium tert-butoxide (8.42 g., 0.075 mole) dissolved in tert-butanol (300 ml.) is added to a refluxing solution of 2-methyl-5-methoxy-6,7-dichloro-1-indanone (12.26 g., 0.05 mole), refluxing is continued for 2 hrs., then a suspension of diphenyliodonium chloride (19.0 g., 0.06 mole) in tert-butanol (1 l.) is added and refluxing is continued for 2 hrs. The reaction mixture is cooled to 25° C., 300 ml. water added, and the mixture concentrated to dryness in vacuo to give 4.97 g. of 2-methyl-2-phenyl-5-methoxy-6,7-dichloro-1-indanone which melts at 161°–163° C. after crystallization from benzene: cyclohexane, 1:2.

Elemental analysis for $C_{17}H_{14}Cl_2O_2$: Calc.: C, 63.51; H, 4.39; Found: C, 63.24; H, 4.68.

Step F: 2-Methyl-2-phenyl-5-hydroxy-6,7-dichloro-1-indanone

A stirred mixture of 2-methyl-2-phenyl-5-methoxy-6,7-dichloro-1-indanone (4.94 g., 0.015 mole) and pyridine hydrochloride (50 g.) is heated at 175° C. for one hour, then poured into water (500 ml.). The 2-methyl-2-phenyl-5-hydroxy-6,7-dichloro-1-indanone which separates (2.05 g.) melts at 194°–196° C. after recrystallization from ethanol: water, 2:1.

Elemental analysis for $C_{16}H_{12}Cl_2O_2$: Calc.: C, 62.56; H, 3.94; Found: C, 62.60; H, 4.11.

Step G: (1-Oxo-2-methyl-2-phenyl-6,7-dichloro-5-indanyloxy)acetic acid

A stirred mixture of 2-methyl-2-phenyl-5-hydroxy-6,7-dichloro-1-indanone (2.05 g., 0.0067 mole), potassium carbonate (1.85 g., 0.0134 mole) and ethyl bromoacetate (2.23 g., 0.0134 mole) in dimethylformamide (30 ml.) is warmed at 55°–60° C. for 3 hours, then treated with potassium hydroxide (0.97 g., 0.0147 mole) dissolved in a minimum amount of water in methanol (30 ml.) and heated on a steam bath for 2½ hours. The reaction mixture is poured into water (500 ml.), acidified with 6 N hydrochloric acid and the precipitate collected after trituration with ether-petroleum ether and dried to give 1.31 g. of (1-oxo-2-methyl-2-phenyl-6,7-dichloro-5-indanyloxy)acetic acid which melts at 168°–169° C. on crystallization from acetic acid:water, 1:1.

Elemental analysis for $C_{18}H_{14}Cl_2O_4$: Calc.: C, 59.20; H, 3.86; Found: C, 58.94; H, 4.20.

EXAMPLE 6

Where in Example 5, there is substituted for the 2,3-dichloroanisole of Step A an equivalent amount of 2-chloro-3-methylanisole, 2,3-dimethylanisole and 2-methyl-3-chloroanisole, respectively, the following compounds of this invention are obtained, respectively:

(1-oxo-2,7-dimethyl-2-phenyl-6-chloro-5-indanyloxy)acetic acid (1-oxo-2,6,7-trimethyl-2-phenyl-5-indanyloxy)acetic acid (1-oxo-2,6-dimethyl-2-phenyl-7-chloro-5-indanyloxy)acetic acid

EXAMPLE 7

Preparation of
[1-Oxo-2-(4-chlorophenyl)-2-methyl-6,7-dichloro-5-indanyloxy]acetic acid heminyhydrate

Step A:
2-(4-chlorophenyl)-2-methyl-5-methoxy-6,7-dichloro-1-indanone

Potassium tert-butoxide (2.81 g., 0.025 mole) dissolved in tert-butanol (150 ml.) is added to a refluxing solution of 2-methyl-5-methoxy-6,7-dichloro-1-indanone (4.90 g., 0.02 mole) in tert-butanol (100 ml.)-benzene (200 ml.), refluxing is continued for 3 hours, then 4,4'-dichlorodiphenyliodonium chloride (11.55 g., 0.03 mole) is added and refluxing is continued for 2 hours. The reaction mixture is cooled to 25° C., 100 ml. water added, and the mixture concentrated to dryness in vacuo to give 4.30 g. of 2-(4-chlorophenyl)-2-methyl-5-methoxy-6,7-dichloro-1-indanone which melts at 176°-178° C. after crystallization from cyclohexane:-benzene, 5:1.

Step B:
2-(4-Chlorophenyl)-2-methyl-5-hydroxy-6,7-dichloro-1-indanone

A stirred mixture of 2-(4-chlorophenyl)-2-methyl-5-methoxy-6,7-dichloro-1-indanone (4.15 g., 0.012 mole) and pyridine hydrochloride (40 g.) is heated at 180° C. for one hour, then poured into water (500 ml.). The 2-(4-chlorophenyl)-2-methyl-5-hydroxy-6,7-dichloro-1-indanone which separates (3.11 g.) melts at 211°-213° C. after crystallization from ethanol:water, 1:1.

Elemental analysis for $C_{16}H_{11}Cl_3O_2$: Calc.: C, 56.25; H, 3.25; Found: C, 55.53; H, 3.23.

Step C:
[1-Oxo-2-(4-chlorophenyl)-2-methyl-6,7-dichloro-5-indanyloxy]acetic acid hemihydrate A stirred mixture of 2-(4-chlorophenyl)-2-methyl-5-hydroxy 6,7-dichloro-1-indanone (2.95 g., 0.00863 mole), potassium carbonate (2.26 g., 0.0163 mole) and ethylbromoacetate (2.72 g., 0.0163 mole) in dimethylformamide (50 ml.) is warmed at 55°-60° C. for two hours, then treated with water (50 ml.)-10 N sodium hydroxide solution (2.5 ml., 0.025 mole) and heated at 80° C. for one hour. The reaction mixture is added slowly to water (500 ml.)-12 N hydrochloric acid (10 ml.) to precipitate 1.37 g. of [1-oxo-2-(4-chlorophenyl)-2-methyl-6,7-dichloro-5-indanyloxy]acetic acid hemihydrate which melts at 141°-142° C. after crystallization from acetic acid:water, 1:1.

Elemental analysis for $C_{18}H_{13}Cl_3O_4 \cdot \frac{1}{2}H_2O$: Calc.: C, 52.90; H, 3.45; Cl, 26.03; Found: C, 52.47; H, 3.45; Cl, 26.11.

EXAMPLE 8

Preparation of
[1-Oxo-2-(4-methoxyphenyl)-2-methyl-6,7-dichloro-5-indanyloxy]acetic acid

Step A: 2-Methyl-5-hydroxy-6,7-dichloro-1-indanone

A stirred mixture of 2-methyl-5-methoxy-6,7-dichloro-1-indanone (30.0 g., 0.123 mole) and pyridine hydrochloride (270 g.) is heated at 180° C. for one hour, then poured into water (1500 ml.). The 2-methyl-5-hydroxy-6,7-dichloro-1-indanone which separates (27.6 g.) melts at 224°-230° C. and is used without further purification.

Step B: 2-Methyl-5-benzyloxy-6,7-dichloro-1-indanone

A stirred mixture of 2-methyl-5-hydroxy-6,7-dichloro-1-indanone (27.6 g., 0.12 mole), potassium carbonate (24.9 g., 0.18 mole) and benzyl bromide (21.4 ml., 0.18 mole) in dimethylformamide (100 ml.) is warmed at 55°-60° C. for 2 hrs., then poured into water (1 l.) to precipitate 35.5 g. of 2-methyl-5-benzyloxy-6,7-dichloro-1-indanone which melts at 153°-155° C. after crystallization from benzene:hexane, 3:2.

Elemental analysis for $C_{17}H_{14}Cl_2O_2$: Calc.: C, 63.57; H, 4.39; Found: C, 64.28; H, 4.61.

Step C:
2-(4-Methoxyphenyl)-2-methyl-5-benzyloxy-6,7-dichloro-1-indanone

Potassium tert-butoxide (8.42 g., 0.075 mole) dissolved in tert-butanol (450 ml.) is added to a refluxing solution of 2-methyl-5-benzyloxy-6,7-dichloro-1-indanone (16.1 g., 0.05 mole) in tert-butanol (150 ml.)-benzene (600 ml.), refluxing is continued for 2.5 hrs., then 4,4'-dimethoxydiphenyliodonium chloride (37.66 g., 0.10 mole) is added and refluxing is continued for 3 hrs. The reaction mixture is cooled to 25° C., 500 ml. water added, and the mixture concentrated in vacuo to give a brown oil which on ether extraction, drying over anhydrous magnesium sulfate, removal of the ether and chromatographing of the residue on silica gel with chloroform gives 3.44 g. of 2-(4-methoxyphenyl)-2-methyl-5-benzyloxy-6,7-dichloro-1-indanone which melts at 115°-119° C. and is used without further purification.

Step D:
2-(4-Methoxyphenyl)-2-methyl-5-hydroxy-6,7-dichloro-1-indanone 2-(4-Methoxyphenyl)-2-methyl-5-benzyloxy-6,7-dichloro-1-indanone (3.44 g., 0.008 mole) is catalytically hydrogenated in absolute ethanol (300 ml.) over 5% palladium on carbon (500 mg.) in a Parr apparatus at 25° C. for 4 hrs. The reaction mixture is filtered and concentrated in vacuo to give 2.6 g. of 2-(4-methoxyphenyl)-2-methyl-5-hydroxy-6,7-dichloro-1-indanone which melts at 149°-156° C. and is used without further purification.

Step E:
[1-Oxo-2-(4-methoxyphenyl)-2-methyl-6,7-dichloro-5-indanyloxy]acetic acid A stirred mixture of 2-(4-methoxyphenyl)-2-methyl-5-hydroxy-6,7-dichloro-1-indanone (2.6 g., 0.0077 mole), potassium carbonate (2.14 g., 0.0154 mole) and ethyl bromoacetate (2.58 g., 0.0154 mole) in dimethylformamide (60 ml.) is warmed at 55°-60° C. for 2.5 hrs., then treated with water (60 ml.),-10 N sodium hydroxide solution (3 ml., 0.03 mole) and heated at 100° C. for one hour. The reaction mixture is added slowly to crushed ice-water (600 ml.)-12 N hydrochloric acid (20 ml.) to precipitate 1.69 g. of [1-oxo-2-(4-methoxyphenyl)-2-methyl-6,7-dichloro-5-indanyloxy]acetic acid which melts at 173°-175° C. after crystallization from nitromethane.

Elemental analysis for $C_{19}H_{16}Cl_2O_5$; Calc.: C, 57.74; H, 4.08; Found: C, 57.35; H, 4.31.

EXAMPLE 9

Preparation of [1-Oxo-2-(4-hydroxyphenyl)-2-methyl-6,7-dichloro-5-indanyloxy]acetic acid A stirred mixture of [1-oxo-2-(4-methoxyphenyl)-2-methyl-6,7-dichloro-5-indanyloxy]acetic acid (1.80 g., 0.0046 mole), Example 8, Step E, 48% hydrobromic acid (50 ml.) and acetic acid (50 ml.) is heated at reflux for one hour, then poured into crushed ice-water (800 ml.) to precipitate 900 mg. of [1-oxo-2-(4-hydroxyphenyl)-2-methyl-6,7-dichloro-5-indanyloxy]-acetic acid which melts at 220°-222° C. after crystallization from acetic acid: water, 1:1, and nitromethane.

Elemental analysis for $C_{18}H_{14}Cl_2O_5 \cdot \frac{1}{3}CH_3NO_2$: Calc.: C, 54.84; H, 3.77; N, 1.16; Found: C, 54.38; H, 3.93; N, 0.94.

EXAMPLE 10

Ethyl (1-Oxo-2-methyl-2-phenyl-6,7-dichloro-5-indanyloxy)-acetate

To a solution of (1-oxo-2-methyl-2-phenyl-6,7-dichloro-5-indanyloxy)acetic acid (1.0 g.), obtained from Example 5, in ethanol (10 ml.) is added borontrifluoride etherate (1.0 ml.). The reaction mixture is refluxed for ½ hour, treated with water and cooled to afford the ethyl (1-oxo-2-methyl-2-phenyl-6,7-dichloro-5-indanyloxy)-acetate.

EXAMPLE 11

N-Ethyl-(1-oxo-2-methyl-2-phenyl-6,7-dichloro-5-indanyloxy acetamide

A solution of (1-oxo-2-methyl-2-phenyl-6,7-dichloro-5-indanyloxy)acetic acid (1.0 g.) obtained from Example 5 and thionyl chloride (0.5 ml.) in benzene (20 ml.) is refluxed for one hour. The solvent is distilled at reduced pressure and the residue is treated with benzene (10 ml.) and ethyl amine (1 ml.). After two hours at 25° C. the reaction mixture is poured into water and extracted with ether; the ether extract is washed first with diluted hydrochloric acid then with aqueous sodium bicarbonate. The ether solution is dried over magnesium sulfate evaporated at reduced pressure to afford the desired N-ethyl-(1-oxo-2-methyl-2-phenyl-6,7-dichloro-5-indanyloxy)acetamide.

EXAMPLE 12

Preparation of [1-Oxo-2-(4-fluorophenyl)-2-methyl-6,7-dichloro-5-indanyloxy]acetic acid Step A: 2-(4-Fluorophenyl)-2-methyl-5-methoxy-6,7-dichloro-1-indanone Potassium tert-butoxide (3.38 g., 0.03 mole) dissolved in tert-butanol (150 ml.) is added to a refluxing solution of 2-methyl-5-methoxy-6,7-dichloro-1-indanone (4.90 g., 0.02 mole) in tert-butanol (50 ml.)-benzene (200 ml.), refluxing is continued for 3 hours, then 4,4'-difluorodiphenyliodonium chloride (10.58 g., 0.03 mole) is added and refluxing is continued for 2½ hours. The reaction mixture is cooled to 25° C., 100 ml. water added, and the mixture concentrated to dryness in vacuo to give 1.24 g. of 2-(4-fluorophenyl)-2-methyl-5-methoxy-6,7-dichloro-1-indanone which melts at 163°-170° C. on treatment with ether-hexane and is used without further purification.

Step B: 2-(4-Fluorophenyl)-2-methyl-5-hydroxy-6,7-dichloro-1-indanone

A stirred mixture of 2-(4-fluorophenyl)-2-methyl-5-methoxy-6,7-dichloro-1-indanone (1.2 g., 0.00354 mole) and pyridine hydrochloride (12 g.) is heated at 180° C. for one hour, then poured into water (500 ml.). The 2-(4-fluorophenyl)-2-methyl-5-hydroxy-6,7-dichloro-1-indanone melts at 193°-200° C. and is used without further purification.

Step C: [1-Oxo-2-(4-fluorophenyl)-2-methyl-6,7-dichloro-5-indanyloxy]acetic acid A stirred mixture of 2-(4-fluorophenyl)-2-methyl-5-hydroxy-6,7-dichloro-1-indanone (1.04 g., 0.0032 mole), potassium carbonate (0.885 g., 0.0064 mole) and ethyl bromoacetate (1.07 g., 0.0064 mole) in dimethylformamide (30 ml.) is warmed at 55°-60° C. for 3 hours, then treated with water (30 ml.)-10 N sodium hydroxide solution (1 ml., 0.01 mole) and heated at 80° C. for one hour. The reaction mixture is added slowly to water (500 ml.)-12 N hydrochloric acid (10 ml.) to precipitate 450 mg. of [1-oxo-2-(4-fluorophenyl)-2-methyl-6,7-dichloro-5-indanyloxy]acetic acid which melts at 150°-156° C. after crystallization from ethyl acetate:-hexane, 1:3.

Elemental analysis for $C_{18}H_{13}Cl_2FO_4$: Calc.: C, 56.42; H, 3.42; Cl, 18.50; Found: C, 56.30; H, 3.65; Cl, 18.57.

EXAMPLE 13

Preparation of (1-Oxo-2,2-diphenyl-6,7-dichloro-5-indanyloxy)acetic acid

Step A: 2,2-Diphenyl-5-methoxy-6,7-dichloro-1-indanone

Potassium tert-butoxide (7.0 g., 0.0624 mole) dissolved in tert-butanol (500 ml.) is added to a mixture of 2-phenyl-5-methoxy-6,7-dichloro-1-indanone (9.59 g., 0.0312 mole), diphenyliodonium chloride (39.6 g., 0.125 mole), tert-butanol (1500 ml.) and benzene (500 ml.) at 70 C. during one hour, then stirred at 70° C. for 2 hours. The reaction mixture is concentrated in vacuo to ¼ of its volume, unreacted iodonium salt filtered off, and the remaining liquid concentrated to dryness to give 5.71 g. of 2,2-diphenyl-5-methoxy-6,7-dichloro-1-indanone which melts at 172°–174° C. after crystallization from cyclohexane.

Elemental analysis for $C_{22}H_{16}Cl_2O_2$: Calc.: C, 68.94; H, 4.21; Found: C, 68.99; H, 4.34.

Step B:
2,2-Diphenyl-5-hydroxy-6,7-dichloro-1-indanone

A stirred mixture of 2,2-diphenyl-5-methoxy-6,7-dichloro-1-indanone (5.5 g., 0.014 mole) and pyridine hydrochloride (55 g.) is heated at 175° C. for one half hour, then poured into water (500 ml.). The 2,2-diphenyl-5-hydroxy-6,7-dichloro-1-indanone which separates (4.94 g.) melts at 207°–213° C.

Elemental analysis for $C_{21}H_{14}Cl_2O_2$: Calc.: C, 68.31; H, 3.82; Found: C, 67.86; H, 3.88.

Step C:
(1-Oxo-2,2-diphenyl-6,7-dichloro-5-indanyloxy)acetic acid

A stirred mixture of 2,2-diphenyl-5-hydroxy-6,7-dichloro-1-indanone (4.9 g., 0.0133 mole), potassium carbonate (3.68 g., 0.0266 mole) and ethyl bromoacetate (4.45 g., 0.0266 mole) in dimethylformamide (150 ml.) is warmed at 55°–60° C. for 3.5 hours, then treated with water (150 ml.)-10 N sodium hydroxide solution (7.5 ml., 0.075 mole) and heated at 90° C. for 1.5 hrs. The reaction mixture is added slowly to water (1 l.)-12 N hydrochloric acid (30 ml.) to precipitate 3.60 g. of (1-oxo-2,2-diphenyl-6,7-dichloro-5-indanyloxy)acetic acid which melts at 251°–252° C. after crystallization from first acetic acid, then nitromethane.

Elemental analysis for $C_{23}H_{16}Cl_2O_4$: Calc.: C, 64.65; H, 3.77; Cl, 16.59; Found: C, 64.69; H, 3.94; Cl, 16.73.

EXAMPLE 14
Preparation of (1-Oxo-2,3-diphenyl-2-methyl-6,7-dichloro-5-indanyloxy)acetic acid

Step A: 2′,3′-Dichloro-4′-methoxypropiophenone

A stirred mixture of 2,3-dichloroanisole (177.0 g., 1.0 mole) and propionyl chloride (101.8 g., 1.1 mole) in methylene chloride (600 ml.) is cooled to 5° C. and treated with aluminum chloride (146.7 g., 1.1 mole) during a 1½ hour period. The reaction is allowed to warm to 25° C. and after 16 hours is poured into ice-water (2 l.) and concentrated hydrochloric acid (200 ml.). The organic phase is washed with 10% sodium hydroxide solution and saturated salt solution, and dried over magnesium sulfate. After evaporation of the solvent, the product is crystallized from hexane to give 124.5 g. (53%) of 2′,3′-dichloro-4′-methoxypropiophenone which melts at 51°–54° C.

Step B: 2,3-Dichloro-4-(2-benzylidenemethyl)anisole

To a mixture of 2′,3′-dichloro-4′-methoxypropiophenone (124.5 g., 0.53 mole) and benzaldehyde (54.4 ml., 0.53 mole) dissolved in ethanol (1 l.) is added dropwise 20% sodium hydroxide solution (117.0 ml., 0.59 mole). The product begins to precipitate after three quarters of the base has been added. After two hours at 25° C. the solid product is collected by suction filtration to give 163.2 g. (95%) of 2,3-dichloro-4-(2-benzylidenemethyl)anisole which melts at 137.5°–139° C. after crystallization from ethanol.

Elemental analysis for $C_{17}H_{14}Cl_2O_2$: Calc.: C, 63.57; H, 4.39; Found: C, 63.69; H, 4.49.

Step C:
2-Methyl-3-phenyl-5-methoxy-6,7-dichloro-1-indanone 2,3-Dichloro-4-(2-benzylidenemethyl)anisole (100 g., 0.32 mole) and trifluoroacetic acid (400 ml.) are heated at gentle reflux for 67 hours. The trifluoroacetic acid is removed, the oily residue triturated with ether to give 80.0 g. of 2-methyl-3-phenyl-5-methoxy-6,7-dichloro-1-indanone which on crystallization from benzene melts at 155°–157° C.

Elemental analysis for $C_{17}H_{14}Cl_2O_2$: Calc.: C, 63.57; H, 4.39; Found: C, 63.17; H, 4.59.

Step D:
2,3-Diphenyl-2-methyl-5-methoxy-6,7-dichloro-1-indanone

Sodium methoxide (2.4 g., 0.045 mole) is added portionwise to a stirred mixture of 2-methyl-3-phenyl-5-methoxy-6,7-dichloro-1-indanone (6.44 g., 0.02 mole), diphenyliodonium chloride (31.6 g., 0.1 mole), dry dimethylformamide (200 ml.) and benzene (200 ml.) at 70° C. under nitrogen, and heating at 70° C. is continued for 2 hours. The reaction mixture is poured into water (1.5 l.), the benzene layer separated, dried over anhydrous magnesium sulfate then concentrated in vacuo to give 2.48 g. of 2,3-diphenyl-2-methyl-5-methoxy-6,7-dichloro-1-indanone after trituration with hexane. This material which melts at 197°–207° C. is used without further purification.

Step E:
2,3-Diphenyl-2-methyl-5-hydroxy-6,7-dichloro-1-indanone

A stirred mixture of 2,3-diphenyl-2-methyl-5-methoxy-6,7-dichloro-1-indanone (2.48 g., 0.0065 mole) and pyridine hydrochloride (25 g.) is heated at 175° C. for one hour, then poured into water (500 ml.). The 2,3-diphenyl-2-methyl-5-hydroxy-6,7-dichloro-1-indanone which separates (2.24 g.) melts at 238°–244° C. and is used without further purification.

Step F:
(1-Oxo-2,3-diphenyl-2-methyl-6,7-dichloro-5-indanyloxy)acetic acid A stirred mixture of 2,3-diphenyl-2-methyl-5-hydroxy-6,7-dichloro-1-indanone (2.24 g., 0.00585 mole), potassium carbonate (1.62 g., 0.0117 mole) and ethyl bromoacetate (1.96 g., 0.0117 mole) in dimethylformamide (100 ml.) is warmed at 55°–60° C. for 3 hours, then treated with water (100 ml.)-10 N sodium hydroxide solution (5 ml., 0.05 mole) and heated at 90° C. for 1.5 hours. The reaction mixture is added slowly to water (1 l.)-12 N hydrochloric acid (10 ml.) to precipitate 1.14 g. of (1-oxo-2,3-diphenyl-2-methyl-6,7-dichloro-5-indanyloxy)acetic acid which melts at 203°–205° C. after crystallization from nitromethane.

Elemental analysis for $C_{24}H_{18}Cl_2O_4$: Calc.: C, 65.32; H, 4.11; Found: C, 65.30; H, 4.19.

EXAMPLE 15

Preparation of
(1-Oxo-2-ethyl-2-phenyl-6,7-dichloro-5-indanyloxy)acetic acid

Step A:
2-Ethyl-2-phenyl-5-methoxy-6,7-dichloro-1-indanone

Sodium methoxide (1.24 g., 0.023 mole) is added portionwise to a stirred mixture of 2-phenyl-5-methoxy-6,7-dichloro-1-indanone (4.61 g., 0.015 mole), iodoethane (15.5 ml., 0.15 mole), benzene (60 ml.) and dimethylformamide (60 ml.) under nitrogen in an ice-water bath. The reaction mixture is left to come to ambient temperature over one hour, then poured into water (1 l.), the benzene layer separated, dried over anhydrous magnesium sulfate and concentrated in vacuo to give 3.23 g. of 2-ethyl-2-phenyl-5-methoxy-6,7-dichloro-1-indanone which melts at 139°–141° C. on crystallization from benzene:hexane, 1:1.

Elemental analysis for $C_{18}H_{16}Cl_2O_2$: Calc.: C, 64.49; H, 4.81; Found: C, 64.73; H, 4.99.

Step B:
2-Ethyl-2-phenyl-5-hydroxy-6,7-dichloro-1-indanone

A stirred mixture of 2-ethyl-2-phenyl-5-methoxy-6,7-dichloro-1-indanone (3.01 g., 0.009 mole) and pyridine hydrochloride (35 g.) is heated at 175° C. for one half hour, then poured into water (350 ml.). The 2-ethyl-2-phenyl-5-hydroxy-6,7-dichloro-1-indanone which separates (2.64 g.) melts at 177°–179° C.

Elemental analysis for $C_{17}H_{14}Cl_2O_2$: Calc.: C, 63.57; H, 4.39; Found: C, 63.73; H, 4.81.

Step C:
(1-Oxo-2-ethyl-2-phenyl-6,7-dichloro-5-indanyloxy)acetic acid

A stirred mixture of 2-ethyl-2-phenyl-5-hydroxy-6,7-dichloro-1-indanone (2.6 g., 0.008 mole), potassium carbonate (2.24 g., 0.016 mole) and ethyl bromoacetate (2.71 g., 0.016 mole) in dimethylformamide (40 ml.) is warmed at 55°–60° C. for 2.5 hours, then treated with water (40 ml.)-10 N sodium hydroxide solution (3 ml., 0.03 mole) and heated at 100° C. for one hour. The reaction mixture is added slowly to water (600 ml.)-12 N hydrochloric acid (10 ml.) to give a gummy residue which on ether extraction, drying and concentrating in vacuo gives 2.16 g. of (1-oxo-2-ethyl-2-phenyl-6,7-dichloro-5-indanyloxy)acetic acid which melts at 187°–189° C.

Elemental analysis for $C_{19}H_{16}Cl_2O_4$: Calc.: C, 60.18; H, 4.25; Found: C, 59.76; H, 4.24.

EXAMPLE 16

Preparation of
(1-Oxo-2-cyclopentyl-2-phenyl-6,7-dichloro-5-indanyloxy)acetic acid

Step A:
2-Cyclopentyl-2-phenyl-5-methoxy-6,7-dichloro-b 1-indanone

Sodium methoxide (1.63 g., 0.03 mole) is added portionwise to a stirred mixture of 2-phenyl-5-methoxy-6,7-dichloro-1-indanone (4.61 g., 0.015 mole), cyclopentyl bromide (16 ml., 0.15 mole), benzene (60 ml.) and dimethyl formamide (60 ml.) under nitrogen at 25° C. The reaction mixture is stirred at 25° C. for 16 hours, then poured into water (1 l.), the benzene layer separated, dried over anhydrous magnesium sulfate and concentrated in vacuo leaving a red-brown oily residue which is chromatographed with chloroform on silica gel to give 1.42 g. of 2-cyclopentyl-2-phenyl-5-methoxy-6,7-dichloro-1-indanone which melts at 105°–108° C.

Elemental analysis for $C_{21}H_{20}Cl_2O_2$: Calc.: C, 67.21; H, 5.37; Found: C, 66.88; H, 5.53.

Step B:
2-Cyclopentyl-2-phenyl-5-hydroxy-6,7-dichloro-1-indanone

A stirred mixture of 2-cyclopentyl-2-phenyl-5-methoxy-6,7-dichloro-1-indanone (1.40 g., 0.0037 mole) and pyridine hydrochloride (14 g.) is heated at 175° C. for one half hour, then poured into water (400 ml.). The 2-cyclopentyl-2-phenyl-5-hydroxy-6,7-dichloro-1-indanone which separates (1.1 g.) melts at 161°–170° C. on crystallization from butyl chloride; chloroform, 5:1.

Elemental analysis for $C_{20}H_{18}Cl_2O_2$: Calc.: C, 66.49; H, 5.02; Found: C, 65.52; H, 5.03.

Step C:
(1-Oxo-2-cyclopentyl-2-phenyl-6,7-dichloro-5-indanyloxy)acetic acid

A stirred mixture of 2-cyclopentyl-2-phenyl-5-hydroxy-6,7-dichloro-1-indanone (1.10 g., 0.003 mole), potassium carbonate (0.85 g., 0.006 mole) and ethyl bromoacetate (1.02 g., 0.006 mole) in dimethylformamide (20 ml.) is warmed at 55°–60° C. for 3 hours, then treated with water (20 ml.)-10 N sodium hydroxide solution (1.2 ml., 0.012 mole) and heated at 100° C. for one hour. The reaction mixture is added slowly to water (300 ml.)-12 N hydrochloric acid (5 ml.) to precipitate 680 mg. of (1-oxo-2-cyclopentyl-2-phenyl-6,7-dichloro-5-indanyloxy)acetic acid which melts at 184°–186° C. after crystallization from nitromethane.

Elemental analysis for $C_{22}H_{20}Cl_2O_4$: Calc.: C, 63.02; H, 4.81; Found: C, 62.59; H, 4.86.

EXAMPLE 17

Preparation of
[1-Oxo-2-methyl-2-(4-nitrophenyl)-6,7-dichloro-5-indanyloxy]acetic acid

Step A:
2-Methyl-2-(4-nitrophenyl)-5-methoxy-6,7-dichloro-1-indanone

Amyl nitrate (40 ml.) is added in 10 ml. increments at two hour intervals to 2-methyl-2-phenyl-5-methoxy-6,7-dichloro-1-indanone (9.36 g., 0.03 mole) in polyphosphoric acid (150 g.) at 50°–60° C. with stirring. The total heating period is 8 hours. The reaction mixture is treated with crushed ice-water to precipitate 4.82 g. of 2-methyl-2-(4-nitrophenyl)-5-methoxy-6,7-dichloro-1-indanone which melts at 179°–180° C. after crystallization from butyl chloride Elemental analysis for $C_{17}H_{13}Cl_2NO_4$: Calc.: C, 55.76; H, 3.58; N, 3.82; Found: C, 55.83; H, 3.66; N, 3.85.

Step B:
2-Methyl-2-(4-nitrophenyl)-5-hydroxy-6,7-dichloro-1-indanone

A stirred mixture of 2-methyl-2-(4-nitrophenyl-5-methoxy-6,7-dichloro-1-indanone (4.82 g., 0.013 mole) and pyridine hydrochloride (50 g.) is heated at 175° C. for onehalf hour, then poured into crushed ice-water (1 l.). The 2-methyl-2-(4-nitrophenyl)-5-hydroxy-6,7- dichloro-1-indanone which separates (4.42 g.) melts at 268°–270° C. after crystallization from ethanol.

Elemental analysis for $C_{16}H_{11}Cl_2NO_4$: Calc.: C, 54.57; H, 3.15; N, 3.98; Found: C, 54.18; H, 3.27; N, 4.66.

Step C:
[1-Oxo-2-methyl-2-(4-nitrophenyl)-6,7-dichloro-5-indanyloxy]acetic acid A stirred mixture of 2-methyl-2-(4-nitrophenyl-5-hydroxy-6,7-dichloro-1-indanone (4.4 g., 0.0126 mole), potassium carbonate (3.49 g., 0.0252 mole) and ethyl bromoacetate (4.21 g., 0.0252 mole) in dimethylformamide (150 ml.) is warmed at 55°–60° C. for 3 hours, then treated with water (150 ml.)−10 N sodium hydroxide solution (7.5 ml., 0.075 mole) and heated at 100° C. for 1.5 hours. The reaction mixture is added slowly to water (1 l.)−12 N hydrochloric acid (15 ml.) to precipitate 2.44 g. of [1-oxo-2-methyl-2-(4-nitrophenyl)-6,7-dichloro-5-indanyloxy]acetic acid which melts at 202°–205° C. after crystallization from nitromethane.

Elemental analysis for $C_{18}H_{13}Cl_2NO_6$: Calc.: C, 52.70; H, 3.19; N, 3.41; Found: C, 52.72; H, 3.16; N, 3.30.

EXAMPLE 18

Preparation of
[1-Oxo-2-(4-aminophenyl)-2-methyl-6,7-dichloro-5-indanyloxy]acetic acid

[1-Oxo-2-methyl-2-(4-nitrophenyl)-6,7-dichloro-5-indanyloxy]acetic acid (6.11 g., 0.015 mole) in absolute ethanol (250 ml.)-36 N sulfuric acid (2 ml.) is catalytically hydrogenated over 5% palladium on carbon (500 mg.) in a Parr apparatus. After one hour, the reaction mixture is filtered, then concentrated in vacuo to a 50 ml. volume. Water (200 ml.) is added to precipitate the ethyl ester which is hydrolyzed by refluxing in ethanol (200 ml.), 10 N sodium hydroxide solution (4.5 ml., 0.045 mole) and water (100 ml.) for 1.5 hours. The reaction mixture is cooled, concentrated to ⅓ its volume, filtered, then neutralized with 6 N hydrochloric acid to precipitate 1.09 g. of [1-oxo-2-(4-aminophenyl)-2-methyl-6,7-dichloro-5-indanyloxy]acetic acid which melts at 235°–236° C. dec.

Elemental analysis for $C_{18}H_{15}Cl_2NO_4$: Calc.: C, 56.86; H, 3.98; N, 3.68; Found: C, 56.46; H, 4.04; N, 3.62.

EXAMPLE 19

Preparation of
5-(1-Oxo-2-methyl-2-phenyl-6,7-dichloro-5-indanyloxymethyl)tetrazole

Step A:
(1-Oxo-2-methyl-2-phenyl-6,7-dichloro-5-indanyloxy)acetonitrile

2-Methyl-2-phenyl-5-hydroxy-6,7-dichloro-1-indanone (4.61 g., 0.015 mole), chloroacetonitrile (1.13 g., 0.015 mole), potassium carbonate (2.08 g., 0.015 mole), potassium iodide (0.25 g., 0.0015 mole) and acetone (75 ml.) are heated at reflux for 23 hours. The reaction mixture is cooled to 25° C. and concentrated to dryness in vacuo to give an oily residue which on trituration with water gives 5.12 g. of (1-oxo-2-methyl-2-phenyl-6,7-dichloro-5-indanyloxy)acetonitrile which melts at 163°–165° C. on crystallization from cyclohexane:benzene, 5:1.

Elemental analysis for $C_{18}H_{13}Cl_2NO_2$: Calc.: C, 62.45; H, 3.78; N, 4.05; Found: C, 63.06; H, 4.03; N, 4.03.

Step B:
5-(1-Oxo-2-methyl-2-phenyl-6,7-dichloro-5-indanyloxymethyl)tetrazole (1-Oxo-2-methyl-2-phenyl-6,7-dichloro-5-indanyloxy)acetonitrile (4.87 g., 0.014 mole), sodium azide (1.09 g., 0.0168 mole), ammonium chloride (0.90 g., 0.0168 mole) and dimethylformamide (30 ml.) are heated at 80° C. for 2½ hrs. The reaction mixture is poured into water (500 ml.), the solution filtered and acidified with 6 N hydrochloric acid to precipitate 2.60 g. of 5-(1-oxo-2-methyl-2-phenyl-6,7-dichloro-5-indanyloxymethyl)tetrazole which melts at 227°–229° C. after crystallization from ethanol.

Elemental analysis for $C_{18}H_{14}Cl_2N_4O_2$: Calc.: C, 55.54; H, 3.63; N, 14.39; Found: C, 55.29; H, 3.90; N, 14.40.

EXAMPLE 20

Preparation of
[1-Oxo-2-(4-bromophenyl)-2-methyl-6,7-dichloro-5-indanyloxy]acetic acid Step A: 2,3-Dichloro-4-(4-bromophenyl)acetylanisole To a stirred mixture of 2,3-dichloroanisole (73.5 g., 0.414 mole), 4-bromophenylacetyl chloride (105 g., 0.456 mole) and carbon disulfide (300 ml.) is added portionwise aluminum chloride (60.9 g., 0.456 mole) with cooling at 0°–5° C. The reaction mixture is left at 25° C. for 17 hours, then flushed with nitrogen, and the solid residue treated with crushed ice and 12 N hydrochloric acid (80 ml.) to give 147.7 g. of 2,3-dichloro-4-(4-bromophenyl)acetylanisole which melts at 163°–164.5° C. after crystallization from benzene:hexane, 1:1.

Elemental analysis for $C_{15}H_{11}BrCl_2O_2$: Calc.: C, 48.16; H, 2.96; Found: C, 48.38; H, 3.10.

Step B:
2′,3′-Dichloro-4′-methoxy-2-(4-bromophenyl)acrylophenone

To a suspension of 2,3-dichloro-4-(4-bromophenyl)-acetyl anisole (142.5 g., 0.38 mole) in bis-dimethylaminomethane (325 ml.) under nitrogen is added dropwise acetic anhydride (325 ml.) with cooling to maintain the reaction mixture temperature below 40° C. The reaction mixture is stirred at 25° C. for one hour, then poured into crushed ice-water (4 l.) to precipitate 143 g. of 2′,3′-dichloro-4′-methoxy-2-(4-bromophenyl)acrylophenone which melts at 110°–116° C. after crystallization from benzene:hexane, 1:5.

Elemental analysis for $C_{16}H_{11}BrCl_2O_2$: Calc.: C, 49.78; H, 2.87; Found: C, 49.73; H, 2.88.

Step C:
2-(4-Bromophenyl)-5-methoxy-6,7-dichloro-1-indanone

2′,3′-Dichloro-4′-methoxy-2-(4-bromophenyl)acrylophenone (143 g., 0.37 mole) dissolved in dichloromethane (2 l.) is drizzled into cold 36 N sulfuric acid (1 l.)-dichloromethane (1 l.) in an ice bath over 4 hours. After stirring for an additional half hour, the reaction mixture is slowly added to crushed ice, the dichloromethane layer separated, washed with saturated salt solution, concentrated in vacuo to give 134.8 g. of 2-(4-bromophenyl)-5-methoxy-6,7-dichloro-1-indanone which melts at 202°–203° C. after trituration with water followed by crystallization from benzene:hexane, 1:1.

Elemental analysis for $C_{16}H_{11}BrCl_2O_2$: Calc.: C, 49.78; H, 2.87; Found: C, 50.46; H, 3.07.

Step D:
2-(4-Bromophenyl)-2-methyl-5-methoxy-6,7-dichloro-1-indanone

Sodium methoxide (28.4 g., 0.522 mole) is added to a stirred mixture of 2-(4-bromophenyl)-5-methoxy-6,7-dichloro-1-indanone (134.6 g., 0.348 mole), iodomethane (217 ml., 3.48 mole), dry benzene (1700 ml.) and dry dimethylformamide (1700 ml.) under nitrogen in an ice-water bath. The reaction mixture is left to come to ambient temperature over 2 hours, then poured into water (8 l.) to precipitate 92.2 g. of 2-(4-bromophenyl)-2-methyl-5-methoxy-6,7-dichloro-1-indanone, m.p. 200°–203° C., which is not soluble in the benzene present.

Elemental analysis for $C_{17}H_{13}BrCl_2O_2$: Calc.: C, 51.03; H, 3.28; Found: C, 50.71; H, 3.24.

Step E:
2-(4-Bromophenyl)-2-methyl-5-hydroxy-6,7-dichloro-1-indanone

A stirred mixture of 2-(4-bromophenyl)-2-methyl-5-methoxy-6,7-dichloro-1-indanone (5.0 g., 0.0125 mole) and pyridine hydrochloride (50 g.) is heated at 185° C. for one hour, then poured into crushed ice-water (500 ml.). The 2-(4-bromophenyl)-2-methyl-5-hydroxy-6,7-dichloro-1-indanone which separates (4.68 g.) melts at 221°–223° C. after crystallization from ethanol.

Elemental analysis for $C_{16}H_{11}BrCl_2O_2$: Calc.: C, 49.78; H, 2.87; Found: C, 49.18; H, 2.87.

Step F:
[1-Oxo-2-(4-bromophenyl)-2-methyl-6,7-dichloro-5-indanyloxy]acetic acid A stirred mixture of 2-(4-bromophenyl)-2-methyl-5-hydroxy-6,7-dichloro-1-indanone (4.48 g., 0.0116 mole), potassium carbonate (3.88 g., 0.0232 mole) and ethyl bromoacetate (3.21 g., 0.0232 mole) in dimethylformamide (100 ml.) is warmed at 55°–60° C. for 3 hours, then treated with water (100 ml.)-10 N sodium hydroxide solution (5 ml., 0.05 mole) and heated at 100° C. for 2 hours. The reaction mixture is added slowly to crushed ice-water (1500 ml.)-12 N hydrochloric acid (50 ml.) to precipitate 3.24 g. of [1-oxo-2-(4-bromophenyl)-2-methyl-6,7-dichloro-5-indanyloxy]acetic acid which melts at 171°–172° C. after crystallization from nitromethane followed by acetic acid: water, 3:2.

Elemental analysis for $C_{18}H_{13}BrCl_2O_4$: Calc.: C, 48.68; H, 2.95; Found: C, 48.64; H, 2.93.

EXAMPLE 21

Preparation of
[1-Oxo-2-(4-cyanophenyl)-2-methyl-6,7-dichloro-5-indanyloxy]acetic acid

Step A:
2-(4-Cyanophenyl)-2-methyl-5-methoxy-6,7-dichloro-1-indanone 2-(4-Bromophenyl)-2-methyl-5-methoxy-6,7-dichloro-1-indanone (8.00 g., 0.02 mole), cuprous cyanide (3.94 g., 0.04 mole) and dimethylformamide (100 ml.) are heated at reflux for 8 hours, added to warm sodium cyanide solution (3 g. in 400 ml. water), extracted with benzene, the benzene solution dried over anhydrous magnesium sulfate, then concentrated in vacuo to give an oily residue. Chromatographing with chloroform on silica gel gives 1.13 g. of 2-(4-cyanophenyl)-2-methyl-5-methoxy-6,7-dichloro-1-indanone melting at 161°–163° C. after crystallization from benzene:hexane, 2:1.

Elemental analysis for $C_{18}H_{13}Cl_2NO_2$: Calc.: C, 62.45; H, 3.78; N, 4.05; Found: C, 61.37; H, 3.68; N, 3.73.

Step B:
2-(4-Cyanophenyl)-2-methyl-5-hydroxy-6,7-dichloro-1-indanone

A stirred mixture of 2-(4-cyanophenyl)-2-methyl-5-methoxy-6,7-dichloro-1-indanone (2.08 g., 0.006 mole) and pyridine hydrochloride (20 g.) is heated at 185° C. for 2 hours, then poured into ice-water (300 ml.). The 2-(4-cyanophenyl)-2-methyl-5-hydroxy-6,7-dichloro-1-indanone which separates (1.89 g.) melts at 189°–196° C. and is used without further purification.

Step C:
[1-Oxo-2-(4-cyanophenyl)-2-methyl-6,7-dichloro-5-indanyloxy]acetic acid A stirred mixture of 2-(4-cyanophenyl)-2-methyl-5-hydroxy-6,7-dichloro-1-indanone (1.8 g., 0.0054 mole), potassium carbonate (1.5 g., 0.0109 mole) and ethyl bromoacetate (1.8 g., 0.0109 mole) in dimethylformamide (60 ml.) is warmed at 55°–60° C. for 3 hours, then treated with water (60 ml.)-10 N sodium hydroxide solution (3 ml., 0.03 mole) and heated at 100° C. for 1.5 hours. The reaction mixture is added slowly to ice-water (300 ml.)-12 N hydrochloric acid (5 ml.) to precipitate 160 mg. of [1-oxo-2-(4-cyanophenyl)-2-methyl-6,7-dichloro-5-indanyloxy]acetic acid which melts at 184°–5° C. after crystallization from acetic acid: water, 1:1.

Elemental analysis for $C_{19}H_{13}Cl_2NO_4.H_2O$ Calc.: C, 55.90; H, 3.70; N, 3.43; Found: C, 55.77; H, 3.53; N, 4.00.

EXAMPLE 22

Preparation of
[1-Oxo-2-methyl-2-(4-sulfamoylphenyl)-6,7-dichloro-5-indanyloxy]acetic acid

Step A:
[1-Oxo-2-(4-chlorosulfonylphenyl)-2-methyl-6,7-dichloro-5-indanyloxy]acetic acid (1-Oxo-2-methyl-2-phenyl-6,7-dichloro-5-indanyloxy)-acetic acid (0.50 g., 0.0014 mole) is added portionwise with stirring to chlorosulfonic acid (5 ml.) in an ice-water bath. The reaction mixture is stirred at 0° C. for 2 hours, left to come to ambient temperature for 2 hours, then slowly added to crushed ice to precipitate 0.51 g. of [1-oxo-2-(4-chlorosulfonylphenyl)-2-methyl-6,7-dichloro-5-indanyloxy]acetic acid which melts at 209°–210° C. after crystallization from acetic acid:water, 3:2.

Elemental analysis for $C_{18}H_{13}Cl_3O_4S$: Calc.: C, 46.62; H, 2.83; Cl, 22.94; Found: C, 46.67; H, 2.79; Cl, 22.59.

Step B:
[1-Oxo-2-methyl-2-(4-sulfamoylphenyl)-6,7-dichloro-5-indanyloxy]acetic acid

[1-Oxo-2-(4-chlorosulfonylphenyl)-2-methyl-6,7-dichloro-5-indanylxoy]acetic acid (2.0 g., 0.0043 mole) is added portionwise to liquid ammonia with stirring. The ammonia is left to evaporated (3 hours). The residue is dissolved in water (400 ml.), filtered, and acidified with 12 N hydrochloric acid to precipitate 780 mg. of [1-oxo-2-methyl-2-(4-sulfamoylphenyl)-6,7-dichloro-5- indanyloxy]-acetic acid which melts at 258°–260° C. after crystallization from acetic acid.

Elemental analysis for $C_{18}H_{15}Cl_2NO_6S \cdot \frac{1}{4}CH_3CO_2H$: Calc.: C, 48.38; H, 3.51; N, 3.05; Found: C, 48.15; H, 3.52; N, 2.86.

EXAMPLE 23

Process for preparing (1-Oxo-2-methyl-2-phenyl-6,7-dichloro-5-indanyloxy)acetic acid (See British Pat. No. 1,328,528)

A mixture of 1-(1-oxo-2-methyl-2-phenyl-6,7-dichloro-5-indanyloxy)-2-nitroethane (3 g.) and 6 N hydrochloric acid (100 ml.) is refluxed for 16 hours, cooled and extracted with ether. The ether layer is washed with water and extracted with dilute aqueous sodium bicarbonate which upon acidification affords 2.0 g. of (1-oxo-2-methyl-2-phenyl-6,7-dichloro-5-indanyloxy)acetic acid which melts at 168°–169° C.

EXAMPLE 24

Process for preparing (1-oxo-2-methyl-2-phenyl-6,7-dichloro-5-indanyloxy)acetic acid To a suspension of sodium hydride (0.24 g., 0.01 mole) in 1,2-dimethoxyethane (10 ml.) is added a solution of 2-methyl-2-phenyl-5-hydroxy-6,7-dichloro-1-indanone (3.07 g., 0.01 mole) in 1,2-dimethoxyethane (10 ml.) over a 15 minute period. When the evolution of hydrogen ceases diethyl-2-bromomalonate (2.39 g., 0.01 mole) is added and the mixture is refluxed for 1 hour. The solvent is distilled at reduced pressure. The residual diethyl-2-(1-oxo-2-methyl-2-phenyl-6,7-dichloro-5-indanyloxy)malonate is dissolved in ethanol (50 ml.) then water (50 ml.) and sodium bicarbonate (2.5 g.) are added and the mixture is refluxed for four hours, cooled, acidified, extracted with ether, washed with water, and dried over magnesium sulfate.

The ether is evaporated at reduced pressure to give crude 2-(1-oxo-2-methyl-2-phenyl-6,7-dichloro-5-indanyloxy)-malonic acid which is heated at 150° C. until evolution of carbon dioxide ceases affording (1-oxo-2-methyl-2-phenyl-6,7-dichloro-5-indanyloxy)acetic acid which melts at 168°–169° C. after recrystallization from nitromethane.

EXAMPLE 25

Process for preparing (1-oxo-2-methyl-2-phenyl-6,7-dichloro-5-indanyloxy)acetic acid A mixture of (1-oxo-2-methyl-2-phenyl-6,7-dichloro-5-indanyloxy)acetonitrile (3.0 g.), Example 19, Step A, acetic acid (20 ml.), water (5 ml.) and concentrated sulfuric acid (5 ml.) is refluxed for 2 hours then poured into ice-water (100 ml.) affording 2.5 g. of (1-oxo-2-methyl-2-phenyl-6,7-dichloro-5-indanyloxy)acetic acid which melts at 168°–169° C. after recrystallizaion from acetic acid.

EXAMPLE 26

(1,2-Dichloro-5α,5,6,7,8,8α-hexahydro-8α-phenyl-9-oxofluoren-3-yloxy)acetic acid Step A: Cyclohexyl (2,3-dichloro-4-methoxyphenyl) ketone A stirred mixture of 2,3-dichloroanisole (88.5 g., 0.5 mole) and cyclohexanecarbonyl chloride (81 g., 0.55 mole) in methylene chloride (400 ml.) is cooled to 5° C. and treated with aluminum chloride (74 g., 0.55 mole) during a ½ hour period. The reaction is allowed to warm to 25° C. and after 16 hours is poured into ice-water (1 l.) and hydrochloric acid (200 ml.). The organic phase is washed with 10% sodium hydroxide and saturated salt solution, and dried over magnesium sulfate. After evaporation of the solvent, the product is crystallized from hexane to give 42.3 g. of cyclohexyl (2,3-dichloro-4-methoxyphenyl) ketone which melts at 97°–98° C.

Elemental analysis for $C_{14}H_{16}Cl_2O_2$: Calc.: C, 58.55; H, 5.62; Found: C, 58.92; H, 5.64.

Step B: 1-Bromocyclohexyl(2,3-dichloro-4-methoxyphenyl) ketone

Bromine (22.4 g., 0.14 mole) in acetic acid (50 ml.) is added dropwise to a stirred solution of cyclohexyl-(2,3-dichloro-4-methoxyphenyl) ketone (40 g., 0.14 mole) and 30% hydrobromic acid (0.5 ml.) in acetic acid (400 ml.) during a one and one half hour period at 25° C. The mixture is poured into water (1.5 l.) and sodium bisulfite (10 g.). The product which precipitates is crystallized from cyclohexane to give 47.3 g. of 1-bromocyclohexyl(2,3-dichloro-4-methoxyphenyl) ketone which melts at 94°–95° C.

Elemental analysis for $C_{14}H_{15}BrCl_2O_2$: Calc.: C, 45.93; H, 4.13; Found: C, 45.77; H, 4.11.

Step C: 1-Cyclohexenyl(2,3-dichloro-4-methoxyphenyl) ketone

1-Bromocyclohexyl (2,3-dichloro-4-methoxyphenyl) ketone (47.3 g., 0.13 mole), lithium chloride (16.5 g., 0.39 mole) and dimethylformamide (200 ml.) are heated at 90° C. for two hours, then poured into water (1 l.) to give 36.5 g. of 1-cyclohexenyl (2,3-dichloro-4-methoxyphenyl) ketone which melts at 126°–129° C. after drying at 60° C. under vacuum for 16 hours.

Elemental analysis for $C_{14}H_{14}Cl_2O_2$: Calc.: C, 58.96; H, 4.95; Found: C, 58.87; H, 5.10.

Step D: 1α,1,2,3,4,4α-Hexahydro-6-methoxy-7,8-dichlorofluoren-9-one

A stirred mixture of 1-cyclohexenyl(2,3-dichloro-4-methoxyphenyl) ketone (34 g., 0.12 mole) and polyphosphoric acid (340 g.) is heated at 90° C. for 17 hours in a resin pot. Crushed ice (1 kg.) is added to precipitate the product which on crystallization from benzene:cyclohexane, 1:1, gives 18.4 g. of 1α,1,2,3,4,4α-hexahydro-6-methoxy-7,8-dichlorofluoren-9-one which melts at 169°–171° C.

Elemental analysis for $C_{14}H_{14}Cl_2O_2$: Calc.: C, 58.96; H, 4.95; Found: C, 59.35; H, 5.43.

Step E: 1α-phenyl-1α,1,2,3,4,4α-hexahydro-6-methoxy-7,8-dichlorofluoren-9-one

Potassium tert-butoxide (1.69 g., 0.015 mole) in tert-butanol (40 ml.) is added to a refluxing solution of 1α,1,2,3,4,4α-hexahydro-6-methoxy-7,8-dichloro-fluoren-9-one (2.85 g., 0.01 mole) in dry benzene (50 ml.) tert-butanol (10 ml.) under nitrogen and refluxing is continued for 0.5 hours. The reaction mixture is cooled to 25° C., diphenyliodonium chloride (4.75 g., 0.015 mole) is added and refluxing is continued for 2 hours. The reaction mixture is cooled to 25° C., 50 ml. water added, and the mixture concentrated to dryness in vacuo to give 3.0 g. of 1α-phenyl-1α,1,2,3,4,4α-hexahydro-6-methoxy-7,8-dichlorofluoren-9-one which melts at 136°–142° C. and is used without further purification.

Step F:
1α-Phenyl-1α,1,2,3,4,4α-hexahydro-6-hydroxy-7,8-dichlorofluoren-9-one

A stirred mixture of 1α-phenyl-1α,1,2,3,4,4α-hexahydro-6-methoxy-7,8-dichlorofluoren-9-one (3.0 g., 0.0083 mole) and pyridine hydrochloride (30 g.) is heated at 180° C. for 2 hours, then poured into water (800 ml.). The 1α-phenyl-1α,2,3,4,4α-hexahydro-6-hydroxy-7,8-dichlorofluoren-9-one which separates (1.71 g.) melts at 213°–215° C. after crystallization from absolute ethanol.

Elemental analysis for $C_{19}H_{16}Cl_2O_2$: Calc.: C, 65.72; H, 4.64; Found: C, 66.27; H, 4.78.

Step G:
(1,2-Dichloro-5α,5,6,7,8,8α-hexahydro-8α-phenyl-9-oxo-fluoren-3-yloxy)acetic acid A stirred mixture of 1α-phenyl-1α-1,2,3,4,4α-hexahydro-6-hydroxy-7,8-dichlorofluoren-9-one (1.7 g., 0.0049 mole), potassium carbonate (1.36 g., 0.0098 mole) and ethyl bromoacetate (1.64 g., 0.0098 mole) in dimethylformamide (50 ml.) is warmed at 55°–60° C. for 3 hours, then treated with water (50 ml.)-10 N sodium hydroxide solution (2.5 ml., 0.025 mole) and heated at 80° C. for 1.5 hours. The reaction mixture is added slowly to water (500 ml.)-12 N hydrochloric acid (10 ml.) to precipitate 1.51 g. of (1,2-dichloro-5α,5,6,7,8,8α-hexahydro-8α-phenyl-9-oxo-fluoren-3-yloxy)acetic acid which melts at 194°–196° C. after crystallization from acetic acid:water, 1:1.

Elemental analysis for $C_{21}H_{18}Cl_2O_4$: Calc.: C, 62.24; H, 4.48; Found: C, 62.27; H, 4.56.

EXAMPLE 27

Preparation of (1-oxo-2-methyl-2-phenyl-6,7-dichloro-5-indanyloxy)acetic acid

Step A:
Tert-butyl(1-oxo-2-methyl-2-phenyl-6,7-dichloro-5-indanyloxy)acetate

A mixture of 2-methyl-2-phenyl-5-hydroxy-6,7-dichloro-1-indanone (9.2 g., 0.03 mole), potassium carbonate (8.29 g., 0.06 mole) and tert-butyl bromoacetate (6.44 g., 0.033 mole) in dimethylformamide (30 ml.) is stirred at 25° C. for two hours. The reaction mixture is poured into cold water (150 ml.) and the tert-butyl(1-oxo-2-methyl-2-phenyl-6,7-dichloro-5-indanyloxy)acetate which separates is filtered, rinsed with water and dried.

Step B:
(1-Oxo-2-methyl-2-phenyl-6,7-dichloro-5-indanyloxy)acetic acid

A solution of tert-butyl(1-oxo-2-methyl-2-phenyl-6,7-dichloro-5-indanyloxy)acetate (1.0 g., 0.00237 mole) in benzene (25 ml.) is treated with methanesulfonic acid (2 drops) and refluxed for ½ hour. The reaction mixture is treated with cyclohexane (20 ml.) and cooled affording (1-oxo-2-methyl-2-phenyl-6,7-dichloro-5-indanyloxy)acetic acid which is filtered and dried.

EXAMPLE 28

Preparation of [1-Oxo-2-methyl-2-(2-thienyl)-6,7-dichloro-5-indanyloxy]acetic acid Step A: 2,2'-Dithienyl iodonium chloride To acetic anhydride (70 ml.) at −20° C. there is added dropwise with stirring fuming nitric acid (27 ml.), then iodine (25 g., 0.1 mole) and trifluoroacetic acid (47 ml., 0.61 mole). The mixture is left to warm to ambient temperature while the iodine dissolves over 3 hours. The solvent is removed by distillation in vacuo, the pot temperature never exceeding 50° C. The residue is dissolved in acetic anhydride (150 ml.), the solution cooled to −10° C. and a mixture of thiophene (63 ml., 0.08 mole), acetic anhydride (350 ml.) and trifluoroacetic acid (50 ml.) is added dropwise in one hour. After cooling at 5° C. for 17 hours, the mixture is distilled in vacuo, the pot temperature never exceeding 50° C. Water (500 ml.) is added to the residue, the solution filtered and ammonium chloride (21.36 g., 0.4 mole) in water (100 ml.) added to precipitate 26.6 g. of 2,2'-dithienyl iodonium chloride which melts at 235°–236° C. after crystallization from methanol.

Elemental analysis for $C_8H_6ClIS_2$: Calc.: C, 29.24; H, 1.84; Found: C, 28.90; H, 1.92.

Step B:
2-Methyl-2-(2-thienyl)-5-methoxy-6,7-dichloro-1-indanone

Potassium tert-butoxide (5.06 g., 0.045 mole) dissolved in tert-butanol (100 ml.) is added to a refluxing solution of 2-methyl-5-methoxy-6,7-dichloro-1-indanone prepared by the method described in Example 5, Steps A to D, (7.35 g., 0.03 mole) in tert-butanol (150 ml.)-benzene (150 ml.), refluxing is continued for 3 hours under nitrogen, then the mixture is cooled slightly and solid dithienyliodonium chloride (16.5 g., 0.05 mole) is added in one portion. Heating at reflux is continued for 2 hours. The reaction mixture is cooled to 25° C., 100 ml. water added, and the mixture concentrated to dryness in vacuo to give 3.85 g. of 2-methyl-2-(2-thienyl)-5-methoxy-6,7-dichloro-1-indanone which melts at 145°–146.5° C. after trituration with ether and crystallization from benzene:hexane, 1:4.

Elemental analysis for $C_{15}H_{12}Cl_2O_2S$: Calc.: C, 55.06; H, 3.70; Found: C, 55.24; H, 3.77.

Step C:
2-Methyl-2-(2-thienyl)-5-hydroxy-6,7-dichloro-1-indanone

A stirred mixture of 2-methyl-2-(2-thienyl)-5-methoxy-6,7-dichloro-1-indanone (3.65 g., 0.0112 mole) and pyridine hydrochloride (36 g.) is heated at 175° C. for one-half hour, then poured into crushed ice-water (500 ml.). The 2-methyl-2-(2-thienyl)-5-hydroxy-6,7-dichloro-1-indanone which separates (3.37 g.) melts at 224°–226° C. after crystallization from ethanol:water, 2:1.

Elemental analysis for $C_{14}H_{10}Cl_2O_2S$: Calc.: C, 53.69; H, 3.22; Found: C, 53.27; H, 3.36.

Step D:
[1-Oxo-2-methyl-2-(2-thienyl)-6,7-dichloro-5-indanyloxy]acetic acid

A stirred mixture of 2-methyl-2-(2-thienyl-5-hydroxy-6,7-dichloro-1-indanone (3.13 g., 0.01 g., 0.01 mole), potassium carbonate (2.77 g., 0.02 mole) and ethyl bromoacetate (3.34 g., 0.02 mole) in dimethylformamide (40 ml.) is warmed at 55°–60° C. for 2 hours, then treated with water (40 ml.)-10 N sodium hydroxide solution (4 ml., 0.04 mole) and heated at 100° C. for one hour. The reaction mixture is added slowly to crushed ice-water (700 ml.)-12 N hydrochloric acid (10 ml.) to precipitate 1.78 g. of [1-oxo-2-methyl-2-(2-thienyl)-6,7-dichloro-5-indanyloxy]acetic acid which melts at 161°–162° C. after crystallization from nitromethane.

Elemental analysis for $C_{16}H_{12}Cl_2O_4S$: Calc.: C, 51.78; H, 3.24; Cl, 19.10; Found: C, 51.66; H, 3.34; Cl, 19.21.

EXAMPLE 29

When in Example 5, Step A, there is substituted for the 2,3-dichloroanisole an equivalent amount of 2-chloro-3-methylanisole, 2,3-dimethylanisole, 3-methylanisole, or 2-methyl-3-chloroanisole, respectively, and Steps B through D in Example 5 and Steps A through D in Example 28 are employed as described, there is obtained:

[1-oxo-2-(2-thienyl)-2,7-dimethyl-6-chloro-5-indanyloxy]acetic acid;

[1-oxo-2-(2-thienyl)-2,6,7-trimethyl-5-indanyloxy]acetic acid;

[1-oxo-2-(2-thienyl)-2,7-dimethyl-5-indanyloxy]acetic acid;

[1-oxo-2-(2-thienyl)-2,6-dimethyl-7-chloro-5-indanyloxy]acetic acid.

EXAMPLE 30

Where in Example 28, Step A, there is substituted for the thiophene an equivalent amount of 2-methylthiophene, 2-bromothiophene, 2-chlorothiophene, or 2,5-dimethylthiophene, respectively, and Steps B through D are employed as described, there is obtained:

[1-oxo-2-methyl-2-(5-methyl-2-thienyl)-6,7-dichloro-5-indanyloxy]acetic acid;

[1-oxo-2-methyl-2-(5-bromo-2-thienyl)-6,7-dichloro-5-indanyloxy]acetic acid;

[1-oxo-2-methyl-2-(5-chloro-2-thienyl)-6,7-dichloro-5-indanyloxy]acetic acid;

[1-oxo-2-methyl-2-(2,5-dimethyl-3-thienyl)-6,7-dichloro-5-indanyloxy]acetic acid.

EXAMPLE 31

Preparation of [1-Oxo-2-(4-aminomethylphenyl)-2-methyl-6,7-dichloro-5-indanyloxy]acetic acid Step A:
{1-Oxo-2-[4-(2-chloroacetamidomethyl)-phenyl]-2-methyl-6,7-dichloro-5-indanyloxy}acetic acid Well-pulverized N-hydroxymethyl-2-chloroacetamide (3.37 g., 0.0274 mole) is added portionwise to (1-oxo-2-methyl-2-phenyl-6,7-dichloro-5-indanyloxy)acetic acid (10.0 g., 0.0274 mole) in 36 N sulfuric acid (100 ml.) and acetic acid (100 ml.) with stirring at 40°–50° C. over one-half hour. Additional N-hydroxymethyl-2-chloroacetamide (1.68 g., 0.014 mole) is added over a four hour period until no starting material remains. After stirring at 25° C. for 16 hours the reaction mixture is added to crushed ice-water (2 l.) to precipitate 11.9 g. of {1-oxo-2-[4-(2-chloroacetamidomethyl)phenyl]-2-methyl-6,7-dichloro-5-indanyloxy}acetic acid which melts at 138°–141° C. and is used in the next step without purification.

Step B:
Ethyl[1-oxo-2-(4-aminomethylphenyl)-2-methyl-6,7-dichloro-5-indanyloxy]acetate hydrochloride {1-Oxo-2-[4-(2-chloroacetamidomethyl)phenyl]-2-methyl-6,7-dichloro-5-indanyloxy}acetic acid (2.0 g., 0.004 mole), absolute ethanol (20 ml.) and 12 N hydrochloric acid (7 ml.) are combined and heated at reflux for 3 hours. On cooling to 5° C. 1.14 g. of ethyl[1-oxo-2-(4-aminomethylphenyl)-2-methyl-6,7-dichloro-5-indanyloxy]acetate hydrochloride precipitates and melts at 211°–213° C. after crystallization from ethanol.

Elemental Analysis for $C_{21}H_{21}Cl_2NO_4 \cdot HCl$: Calc.: C, 54.98; H, 4.83; N, 3.05; Found: C, 54.39; H, 4.72; N, 2.76.

Step C:
[1-Oxo-2-(4-aminomethylphenyl)-2-methyl-6,7-dichloro-5-indanyloxy]acetic acid sodium salt Ethyl[1-oxo-2-(4-aminomethylphenyl)-2-methyl-6,7-dichloro-5-indanyloxy]acetate hydrochloride (1.57 g., 0.0034 mole), sodium bicarbonate (1.15 g., 0.0136 mole), absolute ethanol (50 ml.) and water (50 ml.) are combined and heated at reflux for 1.5 hours leaving a solution which is filtered, then neutralized with 1 N hydrochloric acid (10.26 ml., 0.01026 mole) to precipitate 900 mg. of [1-oxo-2-(4-aminomethylphenyl)-2-methyl-6,7-dichloro-5-indanyloxy]acetic acid sodium salt which melts at 270°–271° C. after drying.

Elemental Analysis for $C_{19}H_{17}Cl_2NO_4Na$: Calc.: C, 54.83; H, 3.87; N, 3.37; Found: C, 55.07; H, 4.27; N, 3.20.

EXAMPLE 32

Resolution of the Optical Isomers of (1-Oxo-2-methyl-2-phenyl-6,7-dichloro-5-indanyloxy)acetic acid Step A: (+)-isomer A mixture of racemic (1-oxo-2-methyl-2-phenyl-6,7-dichloro-5-indanyloxy)acetic acid (26 g., 0.071 mole) and L-(−)-α-methylbenzylamine (8.6 g., 0.071 mole) is dissolved in hot acetonitrile (250 ml.) and aged at 25° C. for 18 hours.

The acetonitrile is decanted from the resultant salt (13.2 g.) which is thrice recrystallized from a minimum volume of 2-propanol affording 1.9 g. of salt of the pure (+) enantiomer which is converted to the acid by treatment of the salt with dilute hydrochloric acid and ether. The ether phase is washed with water, dried over magnesium sulfate and the ether distilled at reduced pressure. The (+)-isomer melts at 163° C. after crystallization from toluene.

$[\alpha]_D^{25} = +88°$. (redone +90°) (C, 2, acetone) Step B: (−)-isomer

By following substantially the procedure described in Step A using as the reactants partially resolved (1-oxo-2-methyl-2-phenyl-6,7-dichloro-5-indanyloxy)acetic acid (15.5 g., 0.042 mole); (obtained from the acetonitrile mother liquor of Step A) and D-(+)-α-methylbenzylamine (5.15 g., 0.042 mole) in acetonitrile (150 ml.) and thrice recrystallizing the resultant salt from a minimum volume of 2-propanol, there is obtained 2.2 g. of the salt of the pure (−)-enantiomer.

The (−)-isomer melts at 164° C. after crystallization from toluene.

$[\alpha]_D^{25} = -88°$ (redone −90°) (C, 2, acetone)

EXAMPLE 32A

Preparation of
[1-oxo-2-(3-hydroxyphenyl)-2-methyl-6,7-dichloro-5-indanyloxy]acetic acid Ethyl(1-oxo-2-phenyl-2-methyl-6,7-dichloro-5-indanyloxy)acetate (18.95 g., 0.05 mole) dissolved in trifluoroacetic acid (100 ml.) is added portionwise at less than 10° C. to a stirred mixture of lead tetrakistrifluoroacetate (0.055 mole) prepared by stirring lead oxide (37.5 g.), trifluoroacetic acid (85 ml.) and trifluoroaceticanhydride (75 g.) at 25° C. for 96 hrs. After stirring the reaction mixture at 25° C. for 6 hours it is poured into crushed ice-water (1 l.) to precipitate 19.7 g. of a mixture of esters which is hydrolyzed by heating at reflux with ethanol (400 ml.) -water (250 ml.)-10 N sodium hydroxide solution (40 ml.) for ¾ hr. On addition to crushed ice-water (1 l.)-12 N hydrochloric acid (50 ml.) a gummy product precipitates, is extracted with ether then concentrated to give 60% of [1-oxo-2-(3-hydroxyphenyl)-2-methyl-6,7-dichloro-5-indanyloxy]acetic acid and 20% of the 4-hydroxyphenyl derivative. Crystallization from acetic acid gives 2.6 g. of [1-oxo-2-(3-hydroxyphenyl)-2-methyl-6,7-dichloro-5-indanyloxy]acetic acid, m.p. 248°–255° C.

Elemental analysis for $C_{18}H_{14}Cl_2O_5$: Calc.: C, 56.71; H, 3.70; Found: C, 56.44; H, 3.82.

As mentioned previously, the novel compounds of this invention are diuretic and saluretic agents. When administered to patients in therapeutic dosages in conventional vehicles, the instant product effectively reduce the amount of sodium and chloride ions in the body, lower dangerous excesses of fluid levels to acceptable levels and in general, alleviate conditions usually associated with edema or fluid retention.

Also as mentioned previously, these compounds are able to maintain the uric acid concentration in the blood at pretreatment levels or even cause a decrease in uric acid concentration. The presence of excess uric acid in the blood can lead to crystallization of uric acid and uric acid salts in the joints causing gout. In addition hyperuricemia in conjunction with hyperlipidemia has been implicated in increasing the risk of sustaining cardiovascular heart disease.

The compounds of this invention can be administered to patients (both animal and human) in a wide variety of therapeutic dosages in conventional vehicles as, for example, by oral administration in the form of a tablet or by intravenous injection. In addition, the compounds may be formulated into suppositories or as a salve for topical administration or they may be administered sublingually. Also, the daily dosage of the products may be varied over a wide range as, for example, in the form of scored tablets containing 0.25, 1, 5, 10, 25, 50, 100, 150, 200, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a [1-oxo-2-aryl or 2-thienyl-2-substituted-5-indanyloxy (or thio)]alkanoic acid (I) of this invention or a suitable salt, ester, amide derivative, 5-tetrazolyl analog thereof, with 149 mg. of lactose and 1 mg. of magnesium stearate and placing the mixture into a No. 1 gelatin capsule. Similarly, by employing more of the active ingredient and less lactose, other dosage forms can be put up in No. 1 gelatin capsules. Should it be necessary compressed tablets, pills, or other desired unit dosages can be prepared to incorporate the compounds of this invention by conventional methods, and, if desired, can be made up as elixirs or as injectable solutions by methods well known to pharmacists. An effective amount of the drug is ordinarily supplied at a dosage level of from about 0.025 mg. to about 20 mg./kg. of body weight. Preferably the range is from about 0.06 mg. to 7 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form. For example, the compounds of this invention can be combined with anti-hypertensive compounds, and particularly with an agent such as methyl-dopa or reserpine. Also a combination or mixture of different indanones of Formula I with each other can be advantageous particularly where one compound has greater diuretic activity and the other has greater uricosuric activity.

The following example is included to illustrate the preparation of a representative dosage form:

EXAMPLE 33

Preparation of dry-filled capsules containing 10 mg. of active ingredient per capsule

|  | Per Capsule |
| --- | --- |
| (1-Oxo-2-methyl-2-phenyl-6,7-dichloro-5-indanyloxy)acetic acid | 10 mg. |
| Lactose | 189 mg. |
| Magnesium stearate | 1 mg. |
| Capsule (Size No. 1) | 200 mg. |

The (1-oxo-2-methyl-2-phenyl-6,7-dichloro-5-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by a molar equivalent amount of any of the other novel compounds of this invention.

EXAMPLE 34

Parenteral Solution of Sodium
(1-oxo-2-methyl-2-phenyl-6,7-dichloro-5-indanyloxy)acetate (1-Oxo-2-methyl-2-phenyl-6,7-dichloro-5-indanyloxy)acetic acid (1 gm.) is treated with sodium bicarbonate (0.25 gm.) in water (10 ml.) and the mixture stirred and heated to effect solution. The solution is diluted with water to a volume of 50 ml. and sterilized by autoclaving at 120° C. for one hour.

EXAMPLE 35

Dry-filled capsules containing 10 mg. of active ingredient and 0.125 mg. of reserpine per capsule

|  | Per capsule |
| --- | --- |
| (1-Oxo-2-methyl-2-phenyl-6,7-dichloro-5-indanyloxy)acetic acid | 10 mg. |
| Reserpine | 0.125 mg. |

-continued

| | Per capsule |
|---|---|
| Lactose | 188.875 mg. |
| Magnesium stearate | 1 mg. |
| Capsule (size No. 1) | 200 mg. |

The (1-oxo-2-methyl-2-phenyl-6,7-dichloro-5-indanyloxy)acetic acid and reserpine are united and reduced to a No. 60 powder and then lactose and magnesium stearate are passed through a No. 60 bolting cloth onto the powder and the combined ingredients are admixed for ten minutes and then filled into a No. 1 dry gelatin capsule.

Similar dry-filled capsules can be prepared by replacing the indanyloxyacetic acid ingredient of the above example by any of the compounds of this invention.

EXAMPLE 36

Dry-filled capsules containing 10 mg. of active ingredient and 250 mg. of levo-3-(3,4-dihydroxyphenyl)-2-methylalanine

| | Per Capsule |
|---|---|
| (1-Oxo-2-methyl-2-phenyl-6,7-dichloro-5-indanyloxy)acetic acid | 10 mg. |
| Levo-3-(3,4-dihydroxyphenyl)-2-methylalanine | 265 mg. |
| Lactose | 124 mg. |
| Magnesium stearate | 1 mg. |
| Capsule (size No. 0) | 400 mg. |

The (1-oxo-2-methyl-2-phenyl-6,7-dichloro-5-indanyloxy)acetic acid and levo-3-(3,4-dihydroxyphenyl)-2-alanine are united and reduced to a No. 60 powder and then lactose and magnesium stearate are passed through a No. 60 bolting cloth onto the powder and the combined ingredients admixed for ten minutes and then filled into a No. 0 dry gelatin capsule.

It will be apparent from the foregoing description that the 1-oxo-2,2-disubstituted-5-indanyloxyalkanoic acid products (I) of this invention constitute a valuable class of compounds which have not been prepared heretofore. One skilled in the art will also appreciate that the processes disclosed in the above examples are merely illustrative and are capable of a wide variation and modification without departing from the spirit of this invention.

EXAMPLE 37

Dry-filled capsules containing 50 mg. of active ingredient per capsule

| | Per Capsule |
|---|---|
| (1-Oxo-2-methyl-2-(2-thienyl)-6,7-dichloro-5-indanyloxy)-acetic acid | 50 mg. |
| Lactose | 149 mg. |
| Magnesium Stearate | 1 mg. |
| Capsule (Size No. 1) | 200 mg. |

The (1-oxo-2-methyl-2-(2-thienyl)-6,7-dichloro-5-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by a molar equivalent amount of any of the other novel compounds of this invention.

EXAMPLE 38

Parenteral Solution of sodium(1-oxo-2-methyl-2-(2-thienyl)-6,7-dichloro-5-indanyloxy)acetate (1-Oxo-2-methyl-2-thienyl-6,7-dichloro-5-indanyloxy)acetic acid (1 gm.) is treated with sodium bicarbonate (0.25 gm.) in water (10 ml.) and the mixture stirred and heated to effect solution. The solution is diluted with water to a volume of 50 ml. and sterilized by autoclaving at 120° C. for one hour.

EXAMPLE 39

Dry-filled capsules containing 25 mg. of active ingredient and 0.125 mg. of reserpine per capsule

| | Per Capsule |
|---|---|
| (1-Oxo-2-methyl-2-(2-thienyl)-6,7-dichloro-5-indanyloxy)-acetic acid | 25 mg. |
| Reserpine | 0.125 mg. |
| Lactose | 173.875 mg. |
| Magnesium stearate | 1 mg. |
| Capsule (size No. 1) | 200 mg. |

The (1-oxo-2-methyl-2-(2-thienyl)-6,7-dichloro-5-indanyloxy)acetic acid and reserpine are united and reduced to a No. 60 powder and then lactose and magnesium stearate are passed through a No. 60 bolting cloth onto the powder and the combined ingredients are admixed for ten minutes and then filled into a No. 1 dry gelatin capsule.

Similar dry-filled capsules can be prepared by replacing the indanyloxyacetic acid ingredient of the above example by any of the compounds of this invention.

EXAMPLE 40

Dry-filled capsules containing 10 mg. of active ingredient and 250 mg. of levo-3-(3,4-dihydroxyphenyl)-2-methylalanine

| | Per Capsule |
|---|---|
| (1-Oxo-2-methyl-2-(2-thienyl)-6,7-dichloro-5-indanyloxy)-acetic acid | 10 mg. |
| Levo-3-(3,4-dihydroxyphenyl)-2-methylalanine | 250 mg. |
| Lactose | 139 mg. |
| Magnesium stearate | 1 mg. |
| Capsule (Size No. 0) | 400 mg. |

The (1-oxo-2-methyl-2-(2-thienyl)-6,7-dichloro-5-indanyloxy)acetic acid and levo-3-(3,4-dihydroxyphenyl)-2-alanine are united and reduced to a No. 60 powder and then lactose and magnesium stearate are passed through a No. 60 bolting cloth onto the powder and the combined ingredients admixed for ten minutes and then filled into a No. 0 dry gelatin capsule.

It will be apparent from the foregoing description that the [1-oxo-2,2-disubstituted-5-indanyloxy]-alkanoic acid products (I) of this invention constitute a valuable class of compounds which have not been prepared heretofore. One skilled in the art will also appreciate that the

What is claimed is:
1. A compound of the formula:

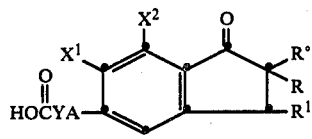

wherein
$R^o$ is

A is oxygen or sulphur;
R is lower alkyl, lower alkenyl, phenyl lower alkyl, phenyl lower alkenyl, phenyl, thienyl, cycloalkyl, or cycloalkyl lower alkyl;
$R^1$ is hydrogen, lower alkyl, or aryl; or
$R^1$ and R may be joined together to form a cycloalkylene;
Y is alkylene or haloalkylene containing from 1 to about 4 carbon atoms;
$X^7$ is hydrogen, loweralkyl or halogen;
$X^8$ is hydrogen or loweralkyl;
$X^1$ is hydrogen, halo or methyl;
$X^2$ is halo, methyl or trihalomethyl; or
$X^1$ and $X^2$ may be joined together to form a hydrocarbylene chain containing from 3 to about 4 carbon atoms;
and the non-toxic, pharmacologically acceptable salt, amide, anhydride and ester derivatives thereof.

2. A compound of the formula:

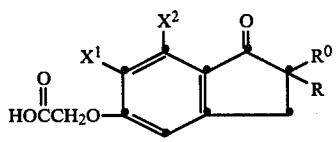

wherein
$R^o$ is

R is lower alkyl;
$X^1$ and $X^2$ are selected from the group consisting of chloro and methyl;
$X^7$ is hydrogen, lower alkyl, halogen or aminomethyl;
$X^8$ is hydrogen or lower alkyl;
and the non-toxic, pharmacologically acceptable salt derivatives thereof.

3. The compound according to claim 2 wherein
$X^7$ is hydrogen; and
$X^8$ is hydrogen.

4. The compound according to claim 3 wherein $R^o$ is

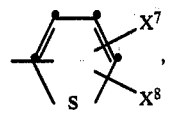

and
$X^7$ and $X^8$ are both hydrogen;
R is methyl;
$X^1$ is chloro;
$X^2$ is chloro
which is [1-oxo-2-(2-thienyl)-2-methyl-6,7-dichloro-5-indanyloxy]acetic acid.

5. A pharmaceutical composition useful in the treatment of edema and hypertension which also maintains uric acid at pretreatment levels or causes a decrease in uric acid levels which comprises a therapeutically effective amount of a compound of the formula:

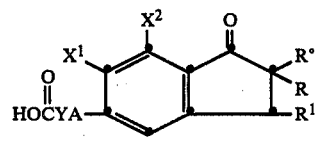

wherein
$R^o$ is

A is oxygen or sulphur;
R is lower alkyl, lower alkenyl, phenyl lower alkyl, phenyl lower alkenyl, phenyl, thienyl, cycloalkyl, or cycloalkyl lower alkyl;
$R^1$ is hydrogen, lower alkyl, or aryl; or
$R^1$ and R may be joined together to form a cycloalkylene;
Y is alkylene or haloalkylene containing from 1 to about 4 carbon atoms;
$X^7$ is hydrogen, lower alkyl or halogen;
$X^8$ is hydrogen or lower alkyl;
$X^1$ is hydrogen, halo or methyl;
$X^2$ is halo, methyl or trihalomethyl; or
$X^1$ and $X^2$ may be joined together to form a hydrocarbylene chain containing from 3 to about 4 carbon atoms;
and the non-toxic, pharmacologically acceptable salt, amide, anhydride, and ester derivatives thereof, and a pharmaceutically acceptable carrier.

6. A pharmaceutical composition useful in the treatment of edema and hypertension which also maintains uric acid at pretreatment levels or causes a decrease which comprises from about 1 mg. to about 500 mg. of a compound of the formula:

[Structure: benzene ring fused with cyclopentanone; substituents X¹, X², HOCCH₂O-, R⁰, R]

wherein
R⁰ is

[Thiophene-like structure with X⁷, X⁸ substituents]

R is lower alkyl;
X¹ and X² are selected from the group consisting of chloro and methyl;
X⁷ is hydrogen, lower alkyl or halogen;
X⁸ is hydrogen or lower alkyl;
a pharmaceutically acceptable salt thereof and a pharmaceutically acceptable carrier.

7. A pharmaceutical composition according to claim 6 wherein
X⁷ is hydrogen and
X⁸ is hydrogen.

8. A method for the treatment of edema, hyperuricemia, and hypertension which comprises administering in a therapeutically effective unitary dosage form a compound of the formula:

[Indanone structure with X¹, X², HOCYA-, R⁰, R, R¹ substituents]

wherein
R⁰ is

[Thiophene structure with X⁷, X⁸]

A is oxygen or sulphur;
R is lower alkyl, lower alkenyl, phenyl lower alkyl, phenyl lower alkenyl, phenyl, thienyl, cycloalkyl or cycloalkyl lower alkyl;
R¹ is hydrogen, lower alkyl or aryl; or
R¹ and R may be joined together to form a cycloalkylene;
Y is alkylene or haloalkylene containing from 1 to about 4 carbon atoms;
X⁷ is hydrogen, lower alkyl or halogen;
X⁸ is hydrogen or lower alkyl;
X¹ is hydrogen, halo or methyl;
X² is halo, methyl or trihalomethyl; or
X¹ and X² may be joined together to form a hydrocarbylene chain containing from 3 to about 4 carbon atoms;
and the non-toxic, pharmacologically acceptable salt, amide, anhydride and ester derivatives thereof.

9. A method of treatment of edema, hyperuricemia and hypertension which comprises administering in unitary dosage form from about 1 mg. to about 500 mg. of a compound or a pharmaceutically acceptable salt thereof of the formula:

[Indanone structure with X¹, X², HOCCH₂O-, R⁰, R]

wherein
R⁰ is

[Thiophene structure with X⁷, X⁸]

R is lower alkyl
X¹ and X² are selected from the group consisting of methyl or chloro;
X⁷ is hydrogen, lower alkyl or halogen;
X⁸ is hydrogen or lower alkyl.

10. The method of claim 9 wherein
X⁷ is hydrogen; and
X⁸ is hydrogen.

11. A pharmaceutical composition useful in the treatment of edema and hypertension which also maintains uric acid levels at pretreatment levels or causes a decrease in uric acid levels which comprises a therapeutically effective amount of a compound of the formula:

[Indanone structure with X¹, X², HOCYA-, R⁰, R, R¹]

wherein
R⁰ is

[Thiophene structure with X⁷, X⁸]

A is oxygen or sulphur;
R is lower alkyl, lower alkenyl, phenyl lower alkyl, thienyl, phenyl lower alkenyl, phenyl, cycloalkyl or cycloalkyl lower alkyl;
R¹ is hydrogen, lower alkyl or aryl; or
R¹ and R may be joined together to form a cycloalkylene;
Y is alkylene or haloalkylene containing from 1 to about 5 carbon atoms;
X⁷ is hydrogen, lower alkyl or halogen;
X⁸ is hydrogen or lower alkyl;
X¹ is hydrogen, halo or methyl;
X² is halo, methyl or trihalomethyl; or
X¹ and X² may be joined together to form a hydrocarbylene chain containing from 3 to about 4 carbon atoms;
and the non-toxic, pharmacologically acceptable salt, amide, anhydride and ester derivatives thereof and an effective antihypertensive agent along with a pharmaceutically acceptable carrier.

12. A pharmaceutical composition of claim 11 wherein the antihypertensive agent is reserpine.

13. A pharmaceutical composition of claim 11 wherein the antihypertensive agent is levo-3-(3,4-dihydroxyphenyl)-2-methylalanine.

14. A pharmaceutical composition useful in the treatment of edema and hypertension which also maintains uric acid levels at pretreatment levels or causes a decrease in uric acid levels which comprises a therapeutically effective amount of two or more compounds of the formula:

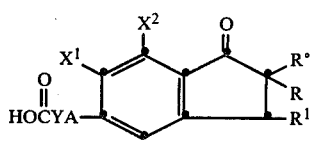

wherein
R$^o$ is

A is oxygen or sulphur;
R is lower alkyl, lower alkenyl, phenyl lower alkyl, thienyl, phenyl lower alkenyl, phenyl cycloalkyl or cycloalkyl lower alkyl;
R$^1$ is hydrogen, lower alkyl or aryl; or
R$^1$ and R may be joined together to form a cycloalkylene;
Y is alkylene or haloalkylene containing from 1 to about 4 carbon atoms;
X$^7$ is hydrogen, lower alkyl or halogen;
X$^8$ is hydrogen or lower alkyl;
X$^1$ is hydrogen, halo or methyl;
X$^2$ is halo, methyl or trihalomethyl; or
X$^1$ and X$^2$ may be joined together to form a hydrocarbylene chain containing from 3 to about 4 carbon atoms;
and the non-toxic, pharmacologically acceptable salt, amide, anhydride and ester derivatives thereof along with a pharmaceutical carrier with the proviso that no two compounds can be exactly the same.

15. A compound of the formula:

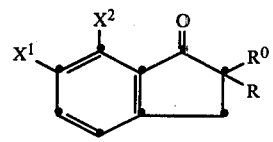

wherein
R$^o$ is

R is lower alkyl or cyclo alkyl from 3 to 6 carbon atoms;
X$^1$ and X$^2$ are selected from the group consisting of chloro and methyl;
X$^7$ is hydrogen or lower alkyl;
X$^8$ is hydrogen;
and the non-toxic pharmaceutically acceptable salt and lower alkyl ester derivative thereof.

16. A compound of the formula

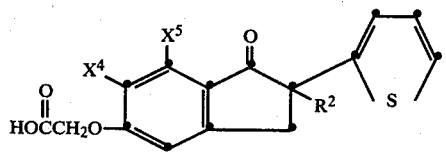

wherein
R$^2$ is lower alkyl from 1 to 3 carbon atoms;
X$^4$ is methyl or chloro;
X$^5$ is methyl or chloro;
and the non-toxic pharmaceutically acceptable salts thereof.

17. The compound according to claim 16 wherein X$^4$ and X$^5$ are both chloro.

18. A compound according to claim 16 wherein R$^2$ is methyl.

* * * * *